US 011389159B2

(12) United States Patent
Nicholas et al.

(10) Patent No.: US 11,389,159 B2
(45) Date of Patent: Jul. 19, 2022

(54) POWERED SURGICAL TACK APPLIER

(71) Applicant: Covidien LP, Mansfield, MA (US)

(72) Inventors: David A. Nicholas, Trumbull, CT (US); Russell V. Pribanic, Roxbury, CT (US)

(73) Assignee: COVIDIEN LP, Mansfield, MA (US)

( * ) Notice: Subject to any disclaimer, the term of this patent is extended or adjusted under 35 U.S.C. 154(b) by 70 days.

(21) Appl. No.: 17/089,870

(22) Filed: Nov. 5, 2020

(65) Prior Publication Data

US 2021/0045740 A1 Feb. 18, 2021

Related U.S. Application Data

(63) Continuation-in-part of application No. 16/532,534, filed on Aug. 6, 2019, now Pat. No. 11,234,701.

(60) Provisional application No. 63/087,501, filed on Oct. 5, 2020, provisional application No. 62/734,290, filed on Sep. 21, 2018.

(51) Int. Cl.
| | | |
|---|---|---|
| *A61B 17/068* | (2006.01) | |
| *A61B 17/10* | (2006.01) | |
| *A61B 17/00* | (2006.01) | |
| *A61B 17/064* | (2006.01) | |

(52) U.S. Cl.
CPC ............ *A61B 17/068* (2013.01); *A61B 17/10* (2013.01); *A61B 17/105* (2013.01); *A61B 2017/0042* (2013.01); *A61B 2017/00314* (2013.01); *A61B 2017/00398* (2013.01); *A61B 2017/00734* (2013.01); *A61B 2017/0647* (2013.01)

(58) Field of Classification Search
CPC ..... A61B 17/10; A61B 17/068; A61B 17/105; A61B 2017/00017; A61B 2017/00119; A61B 2017/00398; A61B 2017/0648; A61B 2017/00734

USPC .......................................................... 606/151
See application file for complete search history.

(56) References Cited

U.S. PATENT DOCUMENTS

| | | | |
|---|---|---|---|
| 5,810,882 | A | 9/1998 | Bolduc et al. |
| 5,824,008 | A | 10/1998 | Bolduc et al. |
| 5,830,221 | A | 11/1998 | Stein et al. |
| 7,867,252 | B2 | 1/2011 | Criscuolo et al. |
| 8,025,199 | B2 | 9/2011 | Whitman et al. |
| 8,282,670 | B2 | 10/2012 | Shipp |
| 8,414,627 | B2 | 4/2013 | Corradi et al. |

(Continued)

FOREIGN PATENT DOCUMENTS

| | | |
|---|---|---|
| EP | 1382302 B1 | 3/2009 |
| EP | 1908409 B1 | 12/2010 |

(Continued)

OTHER PUBLICATIONS

Extended European Search Report issued in EP Application No. 20211932.7, dated May 28, 2021, 6 pages.

(Continued)

*Primary Examiner* — Katherine M Shi
*Assistant Examiner* — Paige A Codrington

(57) ABSTRACT

A powered surgical tack applier is configured to deploy a surgical tack through tissue or a surgical mesh. The surgical tack applier is articulatable to facilitate placement of the surgical tack to a desired surgical location. The powered surgical tack applier includes a power module that includes a battery, a motor, and a gear box. The power module provides a high-speed/low-toque output and a low-speed/high-torque output.

18 Claims, 15 Drawing Sheets

(56) References Cited

U.S. PATENT DOCUMENTS

| | | |
|---|---|---|
| 8,556,930 B2 | 10/2013 | Ellingwood |
| 8,602,288 B2 | 12/2013 | Shelton, IV et al. |
| 9,445,814 B2 | 9/2016 | Ranucci et al. |
| 9,510,825 B2 | 12/2016 | Alexander et al. |
| 2003/0009441 A1 | 1/2003 | Holsten et al. |
| 2004/0230208 A1 | 11/2004 | Shayani |
| 2008/0086154 A1 | 4/2008 | Taylor et al. |
| 2009/0118776 A1 | 5/2009 | Kelsch et al. |
| 2011/0071578 A1 | 3/2011 | Colesanti et al. |
| 2011/0087240 A1 | 4/2011 | Shipp |
| 2011/0295282 A1 | 12/2011 | Glick et al. |
| 2012/0271285 A1 | 10/2012 | Sholev et al. |
| 2013/0018392 A1 | 1/2013 | Zergiebel |
| 2014/0088349 A1 | 3/2014 | Alexander et al. |
| 2014/0121684 A1 | 5/2014 | Criscuolo et al. |
| 2014/0309666 A1* | 10/2014 | Shelton, IV ..... A61B 17/07207 606/139 |
| 2015/0053746 A1 | 2/2015 | Shelton, IV et al. |
| 2015/0196295 A1* | 7/2015 | Shelton, IV ........... A61B 34/71 227/175.1 |
| 2016/0166255 A1 | 6/2016 | Fischvogt |
| 2018/0042591 A1 | 2/2018 | Russo et al. |
| 2018/0049738 A1* | 2/2018 | Meloul ................ A61B 17/068 |
| 2020/0093492 A1 | 3/2020 | Pribanic et al. |

FOREIGN PATENT DOCUMENTS

| | | |
|---|---|---|
| EP | 2684529 A2 | 1/2014 |
| EP | 2870924 A1 | 5/2015 |
| EP | 2870927 A1 | 5/2015 |
| EP | 2870929 A1 | 5/2015 |
| EP | 3195812 A1 | 7/2017 |
| WO | 9707744 A1 | 3/1997 |
| WO | 200176488 | 10/2001 |
| WO | 2013192107 A1 | 12/2013 |
| WO | 2014064695 A2 | 5/2014 |
| WO | 2016157171 A1 | 10/2016 |
| WO | 2016205183 A1 | 12/2016 |
| WO | 2017066732 A1 | 4/2017 |

OTHER PUBLICATIONS

Extended European Search Report EP14199642.1 dated Sep. 11, 2015, 9 pages.
Extended European Search Report issued in European Patent Application No. 19198755.1, dated Feb. 18, 2020, 8 pages.

* cited by examiner

POWERED SURGICAL TACK APPLIER

CROSS-REFERENCE TO RELATED APPLICATION

This application is a continuation-in-part of U.S. patent application Ser. No. 16/532,534, filed on Aug. 6, 2019, which claims the benefit of and priority to U.S. Provisional Patent Application No. 62/734,290, filed on Sep. 21, 2018, the entire disclosure of which is incorporated by reference herein.

This application also claims the benefit of and priority to U.S. Provisional Patent Application No. 63/087,501, filed on Oct. 5, 2020, the entire disclosure of which is incorporated by reference herein.

BACKGROUND

Technical Field

The disclosure relates to surgical instruments and, more particularly, to a surgical tack applier for attaching a prosthesis in place in the repair of a defect in tissue such as an inguinal hernia.

Background of Related Art

Various surgical procedures require instruments capable of applying fasteners to tissue to form tissue connections or to secure objects to tissue. For example, during hernia repair it is often desirable to fasten a mesh to tissue. In certain hernias, such as direct or indirect inguinal hernias, a part of the intestine protrudes through a defect in the abdominal wall to form a hernial sac. The defect may be repaired using an open surgery procedure in which a relatively large incision is made and the hernia is closed outside the abdominal wall by suturing. The mesh is attached with sutures over the opening in the abdominal wall to provide reinforcement. However, this may also be accomplished through the use of minimally invasive surgical fasteners such as, e.g., surgical tacks.

Accordingly, a need exists for a surgical tack applier including a reusable power module that meets performance requirements of various surgical instruments, while inhibiting premature ejection of tacks and timing issues when attempting to eject tacks.

SUMMARY

The disclosure describes a device for applying surgical tacks that demonstrates a practical approach to meeting the performance requirements and overcoming usability challenges associated with applying surgical tacks through a surgical mesh and into tissue.

In accordance with the disclosure, a handle assembly for use with a surgical tack applier includes an actuation assembly and an articulation lever assembly. The actuation assembly includes a motor, an actuation rod, and an actuation switch configured to actuate the motor. In particular, the actuation rod has a first end operatively coupled to an output shaft of the motor for concomitant rotation therewith, and a second end operatively coupled to a loading unit of the surgical tack applier such that rotation of the actuation rod ejects a surgical tack from the loading unit. The articulation lever assembly is configured to articulate an articulation portion of the surgical tack applier. The articulation lever assembly includes an articulation rod operatively coupled with an articulation portion of the surgical tack applier such that axial displacement of the articulation rod causes articulation of the articulation portion, and an articulation lever operatively coupled with the articulation rod.

In an aspect, the actuation assembly may further include a processor configured to control the motor.

In another aspect, the actuation assembly may further include an optical motor encoder configured to count turns of the motor output shaft to ensure a proper number of turns are made to insert a surgical tack into tissue. The optical motor encoder may be operatively connected to the actuation rod and the processor.

In another aspect, the actuation assembly may further include an encoder wheel configured to ensure correct clocking of a distal end of the actuation rod relative to the loading unit.

In yet another aspect, the actuation assembly may further include a light emitting diode coupled with the processor to indicate status of ejection of the surgical tack from the loading unit.

In still yet another aspect, the articulation rod may define a transverse bore dimensioned to receive a drive pin coupled with the articulation lever. The drive pin may define a bore dimensioned to receive the actuation rod therethrough.

In an aspect, the handle assembly may further include a battery pack electrically coupled to the motor and the processor.

In an aspect, the actuation assembly may further include a piezoelectric element configured to provide audible tone for proper ejection of the surgical tack from the loading unit.

In another aspect, the handle assembly may further include a housing pivotably supporting the articulation lever.

In yet another aspect, the articulation lever may include a housing portion and an engaging portion slidably disposed on an engaging surface of the housing.

In still yet another aspect, the engaging surface may define an arcuate profile to enable sliding of the engaging portion in an arc.

In still yet another aspect, the articulation lever assembly may include a biasing member configured to bias the engaging portion of the articulation lever away from the housing of the handle assembly.

In another aspect, the housing may include a detent portion configured to secure a position of the articulation lever relative to the housing of the handle assembly.

In an aspect, the articulation lever assembly may further include articulation pivot arms pivotably secured to the housing of the handle assembly. The articulation pivot arms may be configured to receive the biasing member therebetween.

In another aspect, the articulation pivot arms may be received in the housing portion of the articulation lever.

In yet another aspect, the articulation rod may define a lumen dimensioned to receive the actuation rod therethrough.

In accordance with another aspect of the disclosure, a surgical tack applier includes a handle assembly and an elongate member. The handle assembly includes an actuation assembly and an articulation lever assembly. The actuation assembly includes a motor, an actuation rod having a first end operatively coupled to an output shaft of the motor for concomitant rotation therewith, and an actuation switch configured to actuate the motor. The articulation lever assembly includes an articulation rod and an articulation lever operatively coupled with the articulation rod. The elongate member extends distally from the handle assembly. The elongate member includes a loading unit having a plurality of surgical tacks, and an articulation portion configured to pivot with respect to a longitudinal axis defined by the elongate member. The articulation rod is operatively coupled with the articulation portion of the elongate member such that axial displacement of the articulation rod causes articulation of the articulation portion. A second end of the actuation rod is operatively coupled to the loading unit such that rotation of the actuation rod ejects a surgical tack from the loading unit. The actuation rod extends through the articulation rod.

In an aspect, the actuation assembly may further include a processor configured to control the motor.

In another aspect, the actuation assembly may further include an optical motor encoder configured to count turns of the motor output shaft to ensure a proper number of turns are made to insert a surgical tack into tissue. The optical motor encoder may be operatively connected to the actuation rod and the processor.

In another aspect, the actuation assembly may include an encoder wheel configured to ensure correct clocking of a distal end of the actuation rod relative to the loading unit.

In accordance with yet another aspect of the disclosure, a power surgical tack applier includes a handle assembly, an elongate member, and a power module. The handle assembly includes an actuation assembly and an articulation lever assembly. The actuation assembly includes an actuation rod and an actuation switch. The articulation lever assembly includes an articulation rod and an articulation lever operatively coupled with the articulation rod. The elongate member extends distally from the handle assembly. The elongate member includes a loading unit and an articulation portion. The loading unit has a plurality of surgical tacks. The loading unit is operatively coupled to the actuation rod of the actuation assembly such that rotation of the actuation rod deploys a surgical tack of the plurality of surgical tacks from the loading unit. The articulation portion is pivotable with respect to a longitudinal axis defined by the elongate member. The articulation portion is operatively coupled to the articulation rod of the handle assembly such that axial displacement of the articulation rod articulates the articulation portion. The power module is removably received in the handle assembly. The power module includes a motor, a battery, and a gear box. The motor is operatively coupled to the actuation rod of the actuation assembly to rotate the actuation rod. The battery is electrically coupled to the motor to supply power to the motor. The gear box includes a main sun gear, a first planetary gear assembly, a second planetary gear assembly, a drive shaft, a third planetary gear assembly, a fourth planetary gear assembly, and a high-speed output. The main sun gear is fixed to an output shaft of the motor for concomitant rotation with the output shaft. The first planetary gear assembly is operably coupled to the main sun gear such that the first planetary gear assembly rotates about a longitudinal axis defined by the output shaft in response to rotation of the main sun gear. The second planetary gear assembly is operably coupled to the first planetary gear assembly such that the second planetary gear assembly rotates in response to the rotation of the first planetary gear assembly. The drive shaft is coupled to the second planetary gear assembly such that the drive shaft rotates with the second planetary gear assembly. The third planetary gear assembly is operably coupled to the second planetary gear assembly such that the third planetary gear assembly rotates in response to the rotation of the second planetary gear assembly. The fourth planetary gear assembly is operably coupled to the third planetary gear assembly such that the fourth planetary gear assembly rotates in response to the rotation of the third planetary gear assembly. The high-speed output is coupled to the drive shaft for concomitant rotation therewith. The high-speed output is operably coupled to the actuation rod of the handle assembly.

In an aspect, the gear box of the power module may further include a high-torque output being non-rotatably coupled to the fourth planetary gear assembly such that the high-torque output rotates with the fourth planetary gear assembly.

In another aspect, the high-speed output may be concentrically disposed within the high-torque output.

In yet another aspect, the high-speed and high-torque outputs may be simultaneously rotatable in response to activation of the motor.

In still yet another aspect, the drive shaft may extend longitudinally through the third and fourth planetary gear assemblies.

In still yet another aspect, the drive shaft may have a proximal end portion fixed to the second planetary gear assembly, and a distal end portion rotatable relative to the high-torque output within the high-torque output.

In an aspect, the high-torque output may define a cavity dimensioned to receive the high-speed output therein.

In another aspect, the actuation assembly may further include a processor configured to control the motor.

In yet another aspect, the actuation assembly may further include an optical motor encoder configured to count number of turns of the output shaft of the motor to ensure a desired number of turns are made to insert a surgical tack into tissue. The optical motor encoder may be operatively connected to the actuation rod and the processor.

In yet another aspect, the actuation assembly may further include an encoder wheel configured to ensure correct clocking of a distal end of the actuation rod relative to the loading unit.

In still yet another aspect, the gear box of the power module may further include an elongate ring gear in engagement with the first, second, third and fourth planetary gear assemblies.

In still yet another aspect, the first, second, third, and fourth planetary gear assemblies may be disposed within the elongate ring gear.

In still yet another aspect, the elongate ring gear may be rotationally fixed relative to the motor.

In accordance with yet another aspect of the disclosure, a powered surgical tack applier includes a handle assembly, an elongate member, and a power module. The handle assembly includes an actuation assembly and an articulation lever assembly. The actuation assembly includes an actuation rod. The articulation lever assembly includes an articulation rod and an articulation lever operatively coupled with the articulation rod. The elongate member extends distally from the handle assembly. The elongate member includes a loading unit and an articulation portion. The loading unit has a plurality of surgical tacks. The loading unit is operatively coupled to the actuation rod of the actuation assembly such that rotation of the actuation rod deploys a surgical tack of the plurality of surgical tacks from the loading unit. The articulation portion is pivotable with respect to a longitudinal axis defined by the elongate member. The articulation portion is operatively coupled to the articulation rod of the handle assembly such that axial displacement of the articulation rod articulates the articulation portion. The power module is removably received in the handle assembly. The power module includes a motor having an output shaft, a main sun gear, a first planetary gear assembly, a second planetary gear assembly, a drive shaft, a high-speed output, and a high-torque output. The main sun gear is fixed to the output shaft and configured to rotate with the output shaft. The first planetary gear assembly is operably coupled to the main sun gear such that the first planetary gear assembly rotates about the longitudinal axis in response to a rotation of the main sun gear. The second planetary gear assembly is operably coupled to the first planetary gear assembly such that the second planetary gear assembly rotates in response to the rotation of the first planetary gear assembly. The drive shaft has a proximal end portion coupled to the second planetary gear assembly for concomitant rotation therewith. The high-speed output is configured to rotate the actuation rod. The high-speed output is coupled to the drive shaft for concomitant rotation therewith. The high-torque output is configured to be operably coupled to a driven member of a surgical end effector. The high-torque output is operably coupled to the motor.

In an aspect, the high-speed output may be concentrically disposed within the high-torque output.

In another aspect, the distal end portion of the drive shaft may be disposed within and rotatable relative to the high-torque output.

In yet another aspect, the high-torque output may define a cavity therein, and the high-speed output may be received in the cavity.

In still yet another aspect, the gear box of the power module may further include a biasing member captured between the high-speed output and an inner surface of the high-torque output.

In an aspect, the biasing member may be configured to distally-bias the high-speed output.

In accordance with still yet another aspect of the disclosure, a handle assembly for use with a powered surgical tack applier includes an actuation assembly, an articulation lever assembly, and a power module. The actuation assembly includes an actuation rod and an actuation switch. The articulation lever assembly includes an articulation rod and an articulation lever operatively coupled with the articulation rod. The power module includes a motor having an output shaft, a battery supplying power to the motor, a printed circuit board in communication with the battery and the motor, and a gear box. The gear box includes a main sun gear fixed to the output shaft, a first planetary gear assembly, a second planetary gar assembly, a drive shaft, a high-torque output, and a high-speed output. The first planetary gear assembly is operably coupled to the main sun gear such that the first planetary gear assembly rotates about the longitudinal axis in response to rotation of the main sun gear. The second planetary gear assembly is operably coupled to the first planetary gear assembly such that the second planetary gear assembly rotates in response to rotation of the first planetary gear assembly. The drive shaft has a proximal end portion non-rotatably coupled to the second planetary gear assembly, and a distal end portion. The drive shaft is configured to rotate with the second planetary gear assembly. The high-torque output is operably coupled to the motor. The high-speed output is coupled to the distal end portion of the drive shaft for concomitant rotation therewith.

In an aspect, the power module may be removably received in a cavity of the handle assembly in a sealing relation.

BRIEF DESCRIPTION OF THE DRAWINGS

Various aspects of the disclosure are described hereinbelow with reference to the drawings, which are incorporated and constitute a part of this specification, wherein.

DETAILED DESCRIPTION

Figure 1:
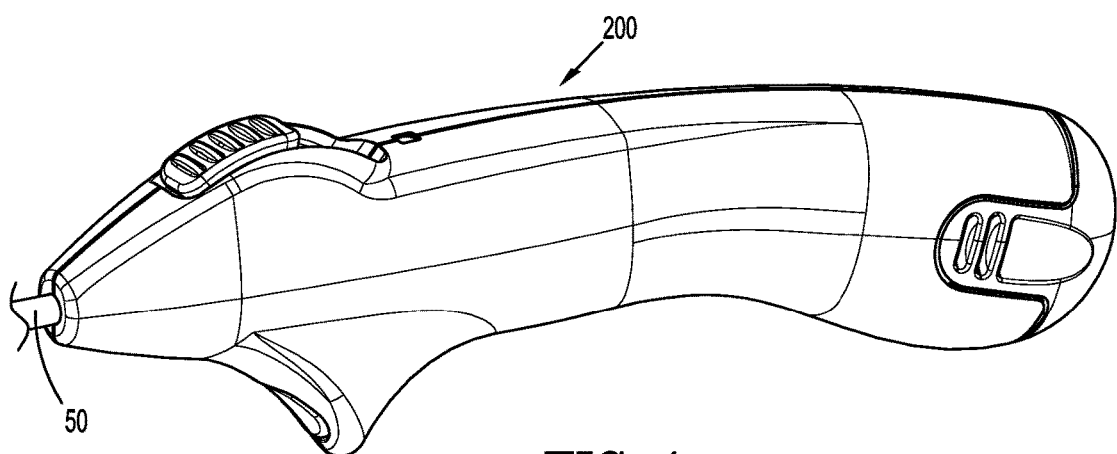
FIG. 1 is a perspective view of a handle assembly of a powered surgical tack applier in accordance with the disclosure.

The disclosed surgical instrument is described in detail with reference to the drawings, in which like reference numerals designate identical or corresponding elements in each of the several views. As used herein, the term "distal," as is conventional, will refer to that portion of the instrument, apparatus, device, or component thereof which is farther from the user, while the term "proximal" will refer to that portion of the instrument, apparatus, device, or component thereof which is closer to the user. In the following description, well-known functions or constructions are not described in detail to avoid obscuring the disclosure in unnecessary detail.

With reference to FIGS. 1-4, a handle assembly for use with a surgical tack applier for applying a surgical tack 10 suitable for insertion through a surgical mesh "M" and tissue "T" is shown generally as a handle assembly 200. The surgical tack applier generally includes the handle assembly 200, an elongate member 50 having an articulation portion 60, and a loading unit 30 selectably connectable to a distal end of the elongate member 50. The loading unit 30 is electro-mechanically coupled to the handle assembly 200 and supports a plurality of surgical tacks 10.

The loading unit 30 includes an outer tube 32 defining a lumen (not shown), a spiral or coil 36 fixedly disposed within the outer tube 32, and an inner tube 38 rotatably disposed within the coil 36. The inner tube 38 defines a lumen therethrough and includes a first portion 38a and a splined second portion 38b. The second portion 38b of the inner tube 38 is slotted, defining a pair of tines 38b1 and a pair of channels 38b2. The second portion 38b of the inner tube 38 is configured to support the plurality of surgical tacks 10 within the inner tube 38. In particular, the surgical tacks 10 are loaded into the loading unit 30 such that the pair of opposing threaded sections 112a of the surgical tacks 10 extend through respective channels 38b2 of the second portion 38b of the inner tube 38 and are slidably disposed within the groove of the coil 36, and the pair of tines 38b1 of the second portion 38b of the inner tube 38 are disposed within the pair of slotted sections 116a of the surgical tack 10. In use, as the inner tube 38 is rotated about a longitudinal axis "X-X" thereof, relative to the coil 36, the pair of tines 38b1 of the inner tube 38 transmits the rotation to the surgical tacks 10 and advance the surgical tacks 10 distally as the head threads 114a of the surgical tacks 10 engage with the coil 36.

Figure 2:
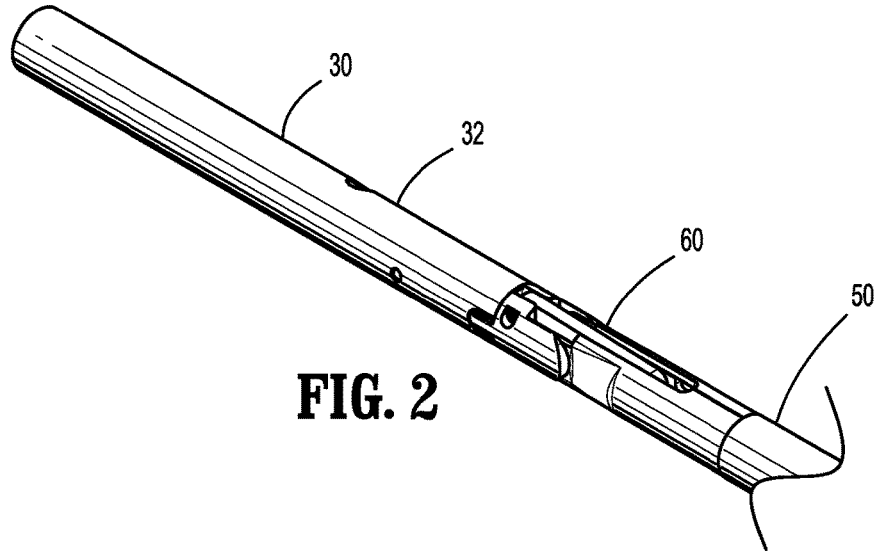
FIG. 2 is a partial perspective view of an elongate member of the powered surgical tack applier.
Figure 3:
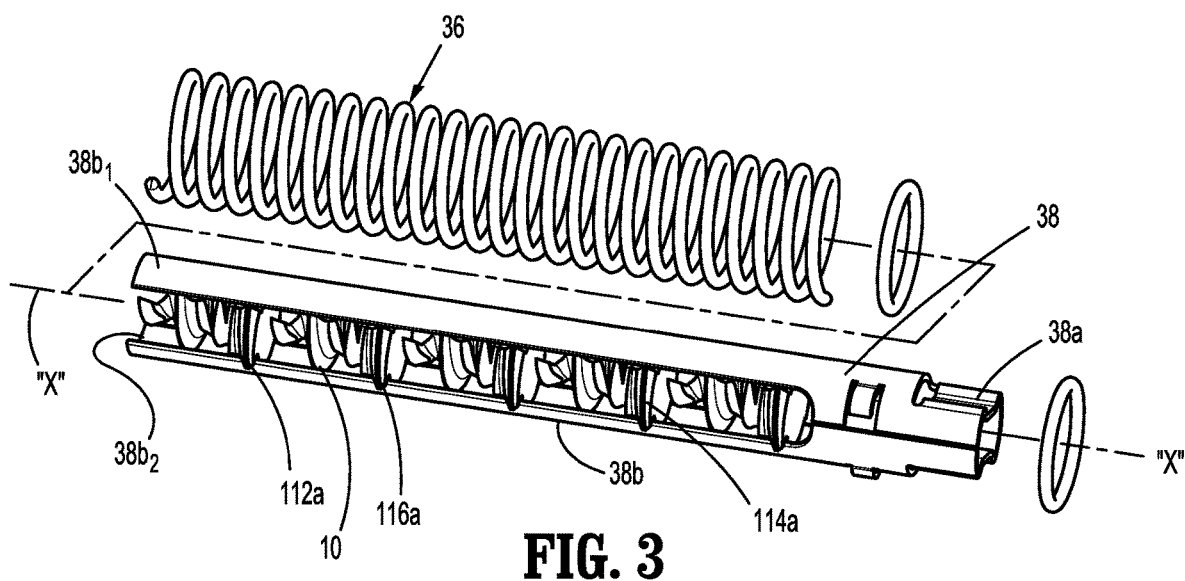
FIG. 3 is a partial perspective view of a loading unit of the surgical tack applier of FIG. 1, illustrating a coil separated from an inner tube.

With particular respect to FIG. 2, the surgical tack applier includes an articulation portion 60 operatively coupled with an articulation lever assembly 300 (FIG. 6) supported in the handle assembly 200. The articulation portion 60 may include a drive assembly (not shown) having a slidable tube and an articulation arm pivotally coupled to the slidable tube. The articulation lever assembly 300 is coupled to the slidable tube so that when the articulation lever assembly 300 is actuated the slidable tube is displaced through the elongated member 50. Longitudinal translation of the slidable tube moves the articulation arm to enable the loading unit 30 to articulate relative to the longitudinal axis "X-X" (FIG. 3). Reference may be made to U.S. Pat. Nos. 7,867,252 and 8,282,670, and U.S. Patent Application Publication No. 2016/0166255, the entire contents of each of which are incorporated herein by reference, for a more detailed discussion of the structure and operation of a surgical tack applier including an articulation portion and a loading unit.

Figure 6:
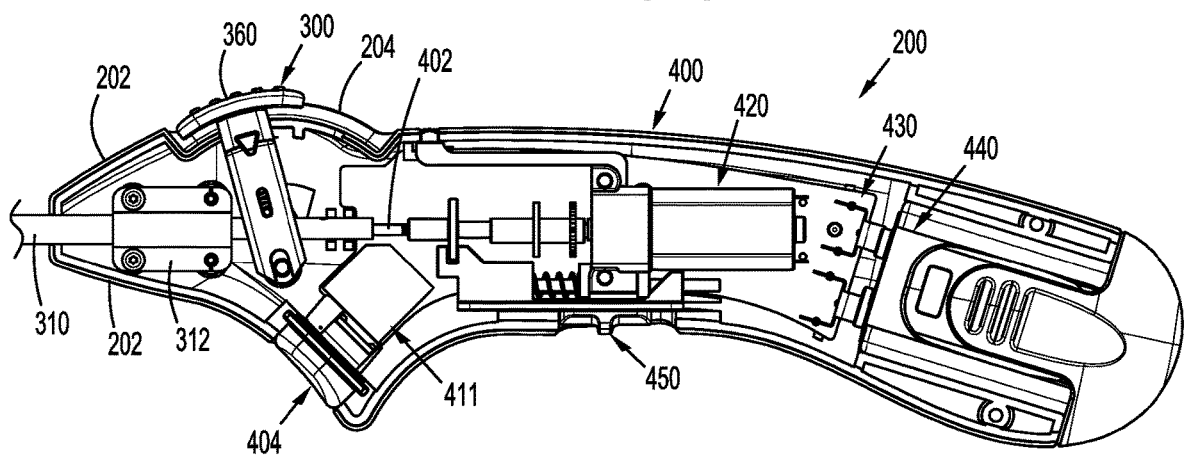
FIG. 6 is a side view of the handle assembly of FIG. 1 with a half of a housing removed.

With reference now to FIG. 6, the handle assembly 200 includes a housing 202, an articulation lever assembly 300 configured to articulate the articulation portion 60 (FIG. 2) of the elongate member 50, an actuation assembly 400 configured to eject the surgical tack 10 out of the loading unit 30 of the elongate member 50, and a battery pack 440 removably attached to the housing 202. The housing 202 includes an ergonomic structure providing comfort, ease of use, and intuitiveness such that when the housing 202 is gripped by a clinician, e.g., a thumb, may be positioned to slide the articulation lever assembly 300 and, e.g., an index finger, may be positioned to trigger an actuation switch 404 of the actuation assembly 400. Actuation of the actuation assembly 400 ejects a surgical tack 10 (FIG. 4) out of the loading unit 30 through mesh "M" (FIG. 4) and into body tissue "T".

Figure 7:
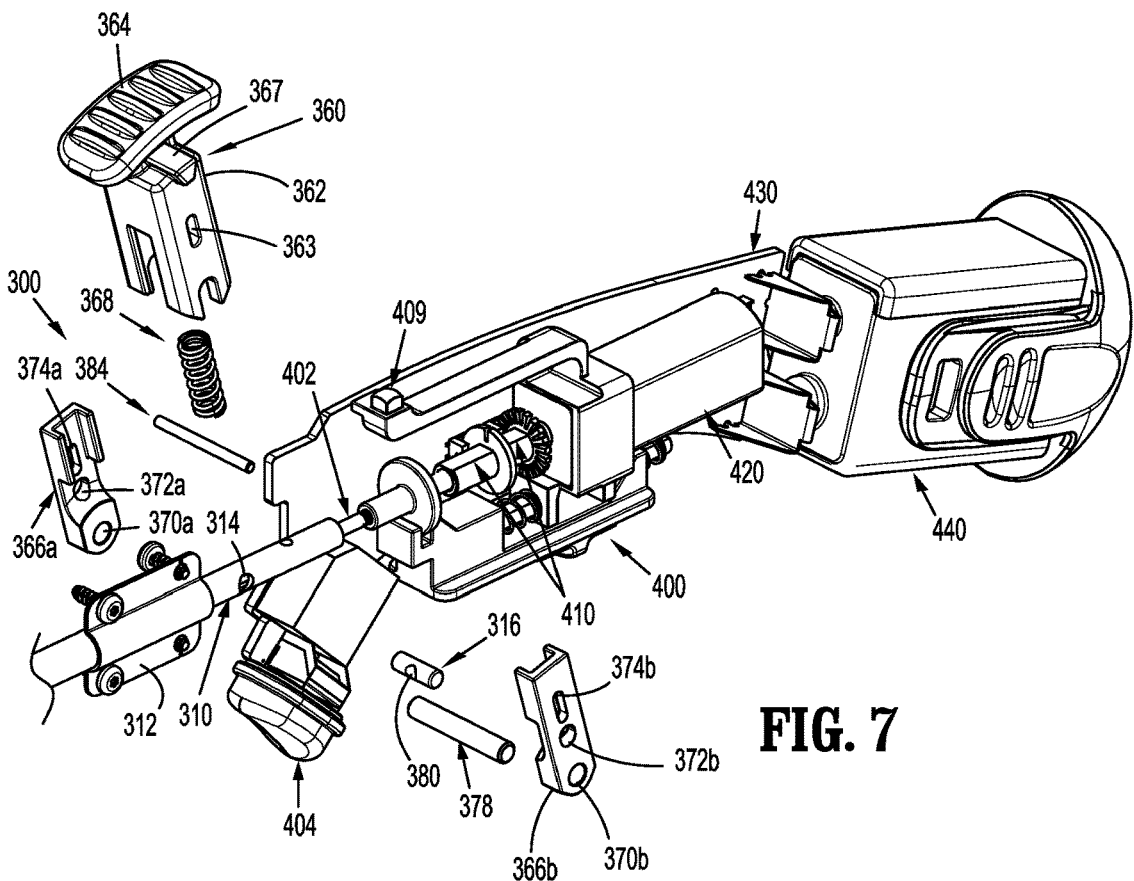
FIG. 7 is an exploded perspective view of the handle assembly of FIG. 1 with parts separated.

With reference to FIGS. 6 and 7, the articulation lever assembly 300 includes an articulation rod 310 and articulation lever 360 operatively coupled with the articulation rod 310. The articulation rod 310 is operatively coupled with the articulation portion 60 (FIG. 2) of the elongate member 50 of the surgical tack applier. The articulation rod 310 is slidably supported on the housing 202 of the handle assembly 200 by a mounting plate 312 defining a channel 304 (FIG. 8) configured to enable axial displacement of the articulation rod 310 therethrough, which, causes articulation of the articulation portion 60 (FIG. 2) based on the axial position of the articulation rod 310. In particular, the articulation rod 310 has an annular structure defining a channel 317 (FIG. 8) dimensioned to receive the actuation rod 402 of the articulation assembly 400 therein. The articulation rod 310 further defines a transverse bore 314 dimensioned to receive an articulation drive pin 316 coupled with the articulation lever 360.

With continued reference to FIGS. 6 and 7, the articulation lever 360 includes a housing portion 362 and an engaging portion 364 slidably engaging an engaging surface 204 of the housing 202. The engaging surface 204 has an arcuate profile enabling the engaging portion 364 to travel in, e.g., an arc. The housing portion 362 is disposed within the housing 202 and is dimensioned to receive articulation pivot arms 366a, 366b mated together to receive a biasing member 368 therebetween. Each articulation pivot arm 366a, 366b defines a first bore 370a, 370b, a second bore 372a, 372b, and a slot 374a, 374b. The first bores 370a, 370b are dimensioned to receive an articulation pivot pin 378 (FIG. 8) pivotably coupling the articulation pivot arms 366a, 366b to the housing 202. The second bores 372a, 372b are dimensioned to receive the articulation drive pin 316 extending through the transverse bore 314 of the articulation rod 310. Under such a configuration, when the articulation pivot arms 366a, 366b are pivoted about the articulation pivot pin 378, the articulation drive pin 316 causes axial displacement of the articulation rod 310. The articulation drive pin 316 defines a transverse bore 380 dimensioned to receive the actuation rod 402 of the actuation assembly 400 therethrough. The slots 374a, 374b of the articulation pivot arms 366a, 366b are dimensioned to cammingly receive a cam pin 384 biased away from the articulation pivot pin 378 by a biasing member 368 interposed between the articulation pivot arms 366a, 366b.

Figure 8:
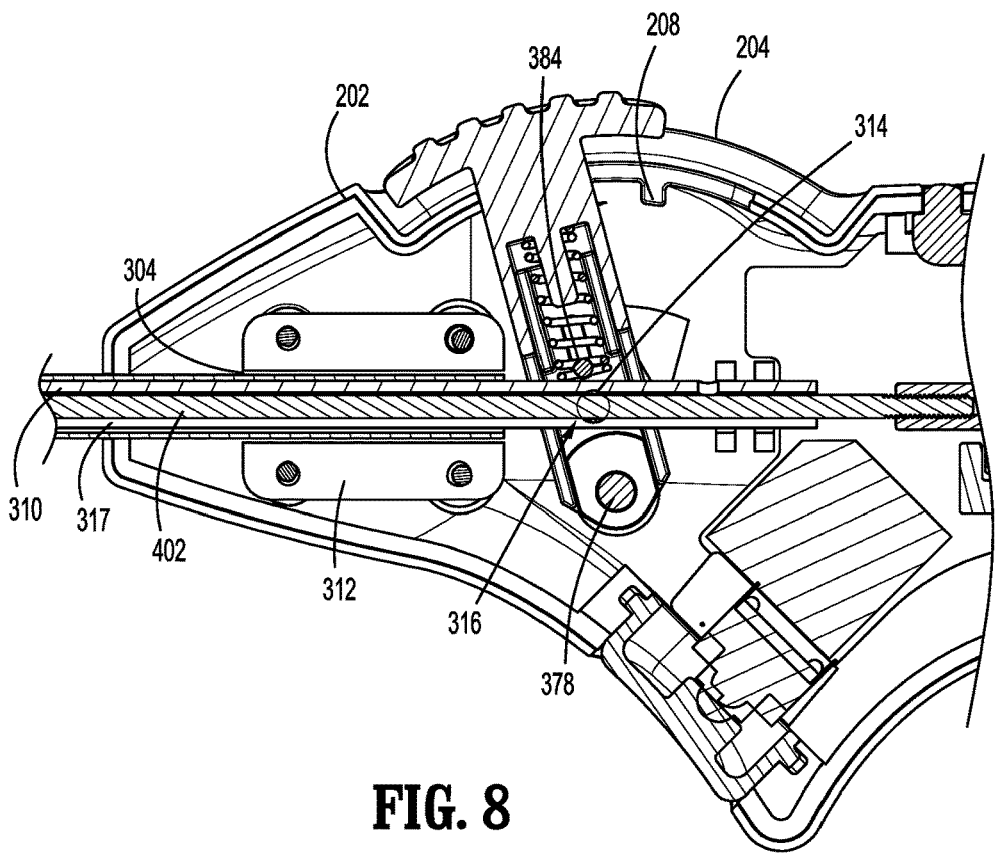
FIG. 8 is a partial side view of the handle assembly of FIG. 1.

With reference now to FIGS. 7 and 8, the housing portion 362 of the articulation lever 360 is dimensioned to receive the mated articulation pivot arms 366a, 366b. The housing portion 362 defines a slot 363 dimensioned to cammingly receive the cam pin 384 which is cammingly slidable in the slots 374a, 374b of the articulation pivot arms 366a, 366b. In addition, the housing portion 362 includes a tooth 367 configured to engage a detent portion 208 of the housing 202 to inhibit movement of the articulation lever 360 relative to the housing 202, thereby locking an axial position of the articulation rod 310, which, in turn, locks the orientation of the articulation portion 60 (FIG. 2) of the surgical tack applier. Under such a configuration, the articulation lever 360 is biased away from the articulation pivot pin 378 such that the tooth 367 of the housing portion 362 engages the detent portion 208. When the engaging portion 364 of the articulation lever 360 is depressed towards the housing 202, the tooth 367 is moved away from the detent portion 208 enabling the clinician to slidably move the engaging portion 364 on the engaging surface 204 (FIG. 6) of the housing 202, thereby enabling articulation of the articulation portion 60 of the surgical tack applier to a desired orientation.

Figure 9:
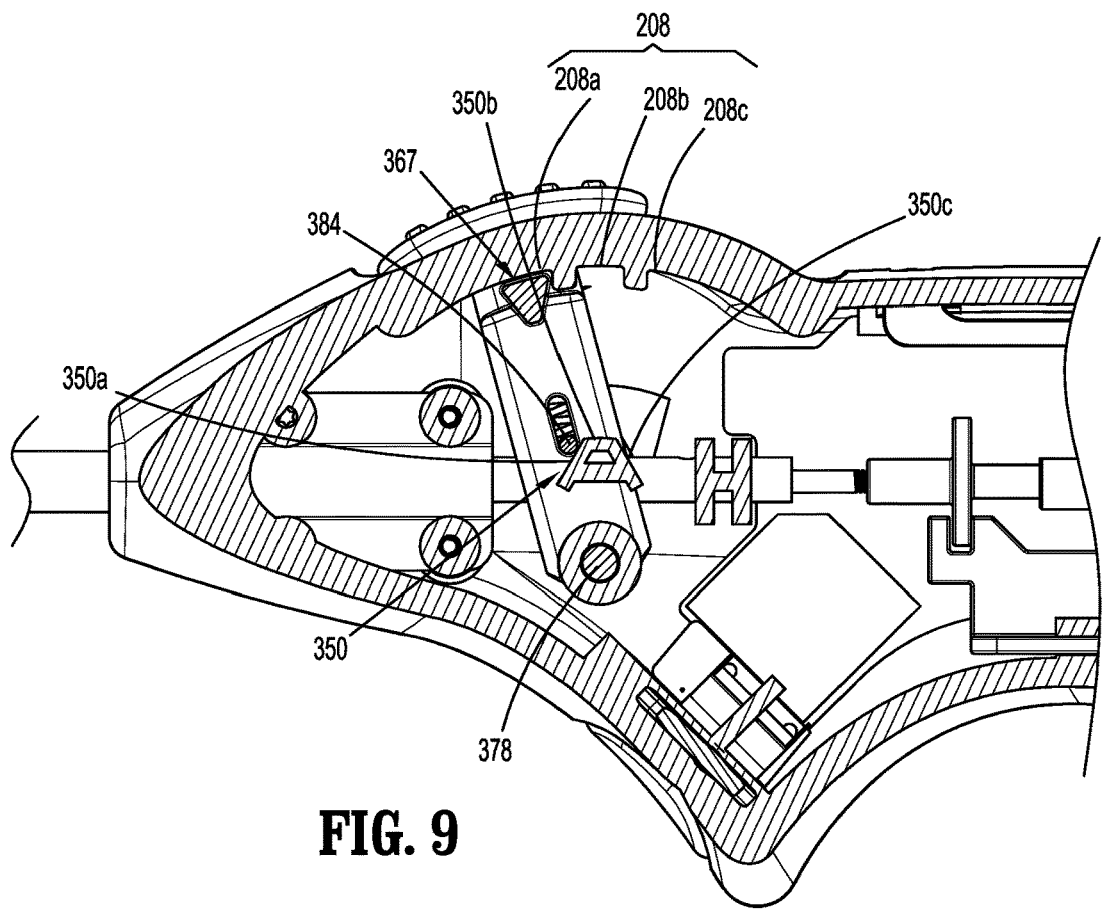
FIG. 9 is a partial side view of the handle assembly of FIG. 1 with a portion of the housing removed.

With reference now to FIG. 9 the articulation lever assembly 300 further includes a cam wedge 350 having first, second, and third portions 350a, 350b, 350c configured to cammingly engage the cam pin 384 which is cammingly slidable in the slots 374a, 374b of the articulation pivot arms 366a, 366b and the slot 363 of the articulation lever 360. The first, second, and third portions 350a, 350b, 350c correspond to the respective detent sections 208a, 208b, 208c of the detent portion 208. In this manner, articulation backlash is reduced as the cam pin 384 rides along the first, second, and third portions 350a, 350b, 350c of the cam wedge 350.

With reference back to FIGS. 6 and 7, the actuation assembly 400 includes an actuation rod 402 operatively coupled with the loading unit 30 (FIG. 2) of the surgical tack applier, a motor 420, an actuation switch 404 configured to actuate the motor 420 to eject the surgical tacks 10 (FIG. 4), a printed circuit board 430 including a microprocessor (not shown) to control the actuation assembly 400, and a battery pack 440 removably attached to the housing 202 and electrically connected to the motor 420 and the printed circuit board 430. A proximal end of the actuation rod 402 is operatively coupled with an output shaft of the motor 420 for concomitant rotation therewith such that when the actuation switch 404 is triggered by the clinician, the motor 420 is actuated to impart axial rotation to the actuation rod 402. A distal end of the actuation rod 402 is operatively coupled with the inner tube 38 (FIG. 3) of the loading unit 30 for concomitant rotation therewith.

Figure 4:
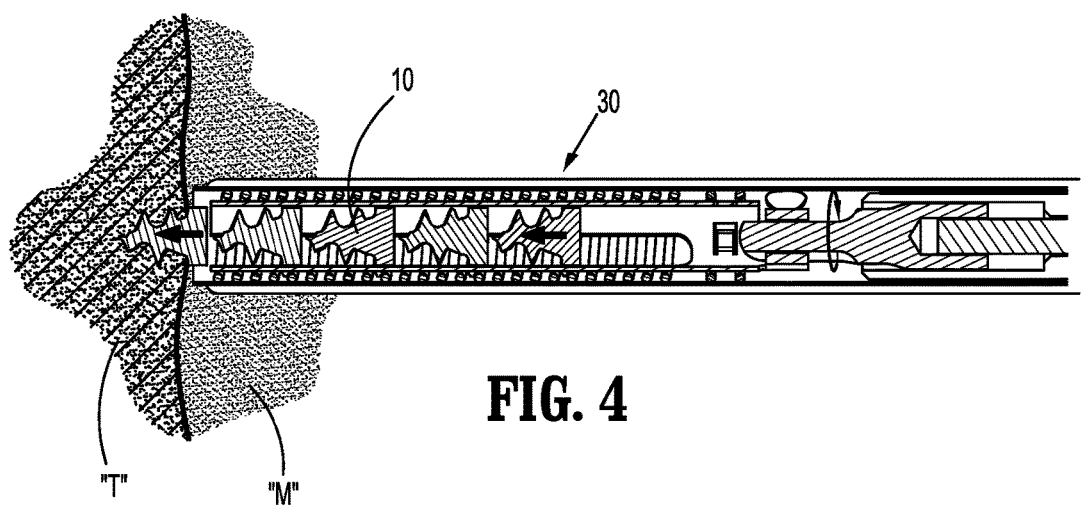
FIG. 4 is a longitudinal, cross-sectional view of a distal end of the powered surgical tack applier, illustrating implanting of a surgical tack into underlying tissue through a surgical mesh.
Figure 10:
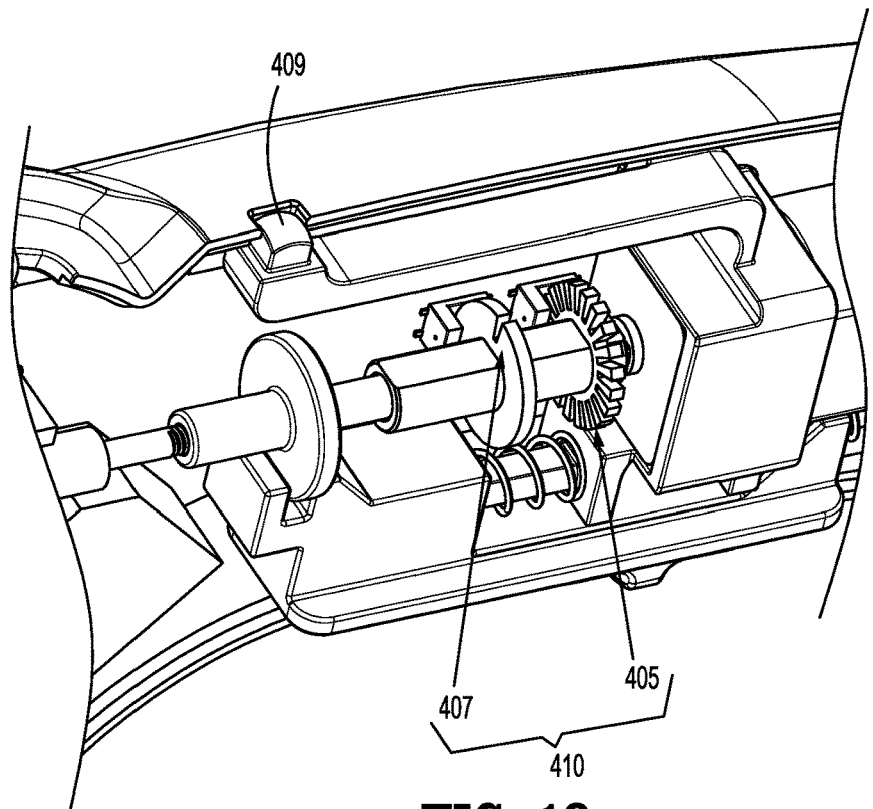
FIG. 10 is a partial perspective view of the handle assembly of FIG. 1, illustrating an actuation assembly.

With reference now to FIG. 10, the actuation assembly 400 may further include an encoder assembly 410 operatively connected to the actuation rod 402 and the processor of the printed circuit board 430. The encoder assembly 410 may include, e.g., an optical, motor encoder 405 configured to keep an accurate count of turns of the motor output shaft or the actuation rod 402 to ensure a proper number of turns are made to insert the surgical tack 10 through, e.g., the mesh "M", and into tissue "T" (FIG. 4). In addition, the encoder assembly 410 may further include, e.g., a single notched, encoder wheel 407 configured to ensure correct clocking of a distal end of the actuation rod 402 relative to the loading unit 30 (FIG. 2). The encoder assembly 410 may further include a light emitting diode ("LED") indicator 409 to indicate status of the ejection of each surgical tack 10. For example, a green light may indicate proper application of the surgical tact 10 through the mesh "M" and into tissue "T", and a red light may indicate, e.g., improper application of the surgical tack 10, due to an error signal from the optical motor encoder 405 or the single notched encoder wheel 407. Alternatively, the encoder assembly 410 may further include a piezoelectric element 411 (FIG. 6) for providing an audible tone for proper application of the surgical tack 10.

With brief reference to FIG. 6, the handle assembly 200 may further include a release lever 450 slidably attached to the housing 202. The release lever 450 is operatively coupled with the loading unit 30 (FIG. 2) such that when the release lever 450 is pulled, the loading unit 30 is detached from the elongate member 50 (FIG. 2) of the surgical tack applier.

Figure 11:
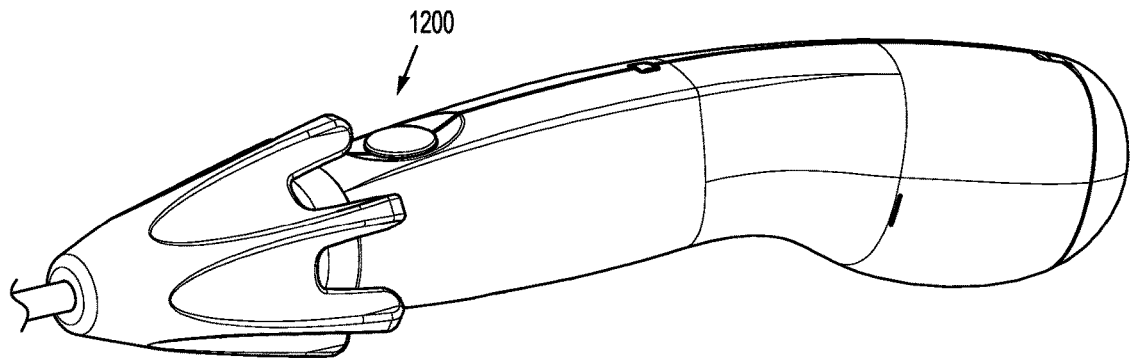
FIG. 11 is a perspective view of a handle assembly for use with a powered surgical tack applier in accordance with another aspect of the disclosure.
Figure 12:
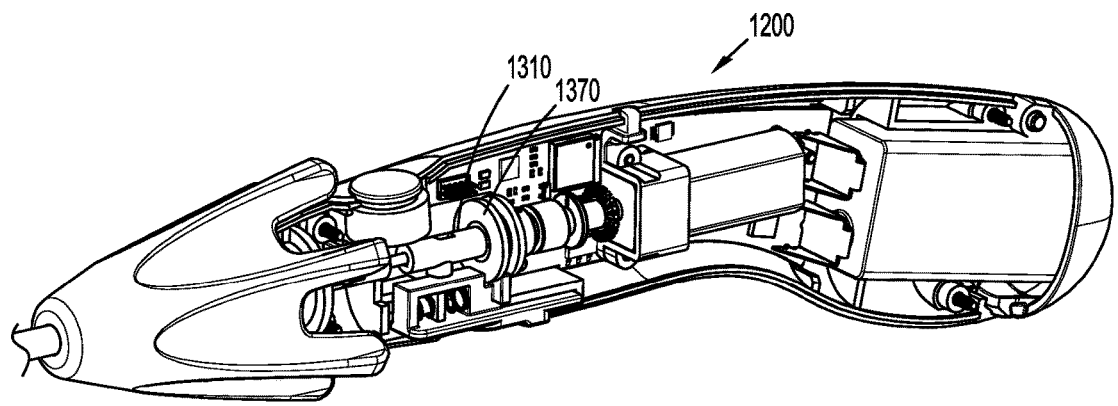
FIG. 12 is a perspective view of the handle assembly of FIG. 11 with a half of the housing removed.
Figure 13:
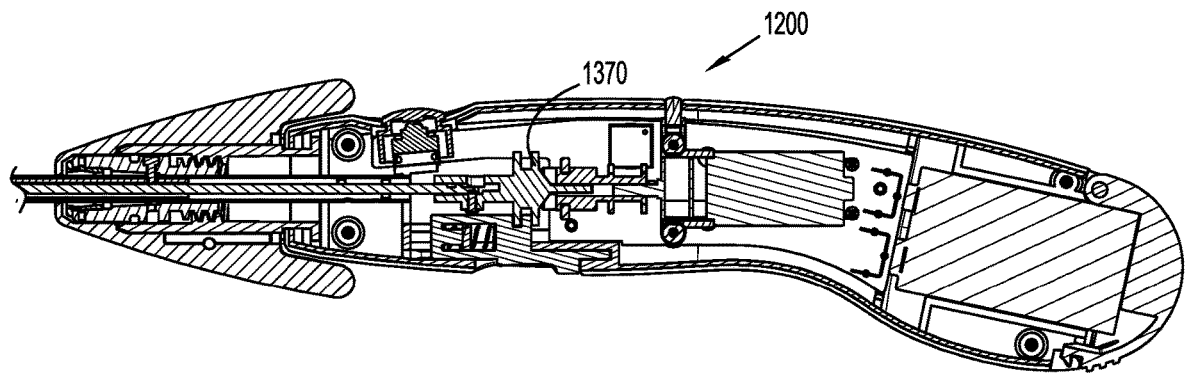
FIG. 13 is a side view of the handle assembly of FIG. 11.

In use, the loading unit 30 is operatively mounted to a distal end of the elongate member 50. The loading unit 30 is introduced into a target surgical site while in the non-articulated condition. The clinician may remotely articulate loading unit 30 relative the longitudinal axis "X-X" to access the surgical site. Specifically, the clinician may slide the engaging portion 364 of the articulation lever 360 along the engaging surface 204 of the housing 202. As the articulation rod 310 is displaced axially, the loading unit 30 is moved to an articulated orientation relative to the central longitudinal axis "X-X". Furthermore, the clinician may position the surgical mesh "M" adjacent the surgical site. Once the surgical mesh "M" is properly positioned on the surgical site, the clinician may trigger the actuation switch 404 to eject a surgical tack 10 through the mesh "M" and into tissue "T". While the articulation rod 310 is configured for axial displacement, it is further contemplated that an articulation rod 1310 may be rotatably supported by a rotor 1370 such that the articulation rod 1310 outputs an axial rotation which may be utilized by the loading unit 30 to effect articulation thereof, as can be appreciated with reference to FIGS. 11-13. It is further contemplated that the articulation assembly 400 may further include a transmission assembly to selectively impart rotation of the output shaft of the motor 420 to the actuation rod 1310.

Figure 14:
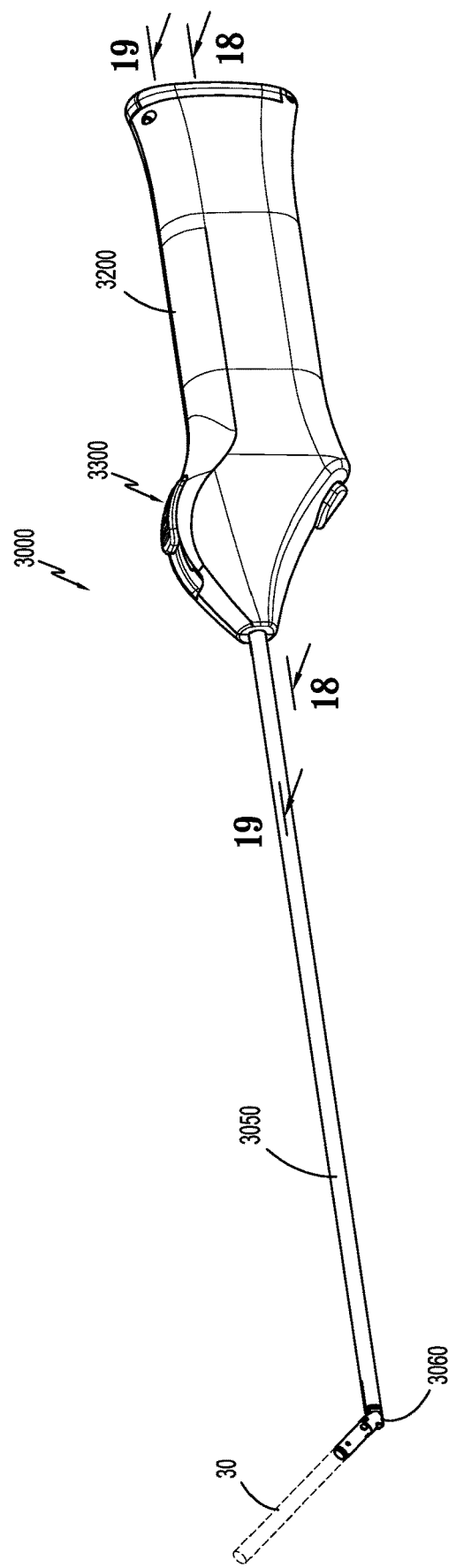
FIG. 14 is a perspective view of a powered surgical tack applier in accordance with another aspect of the disclosure.
Figure 15:
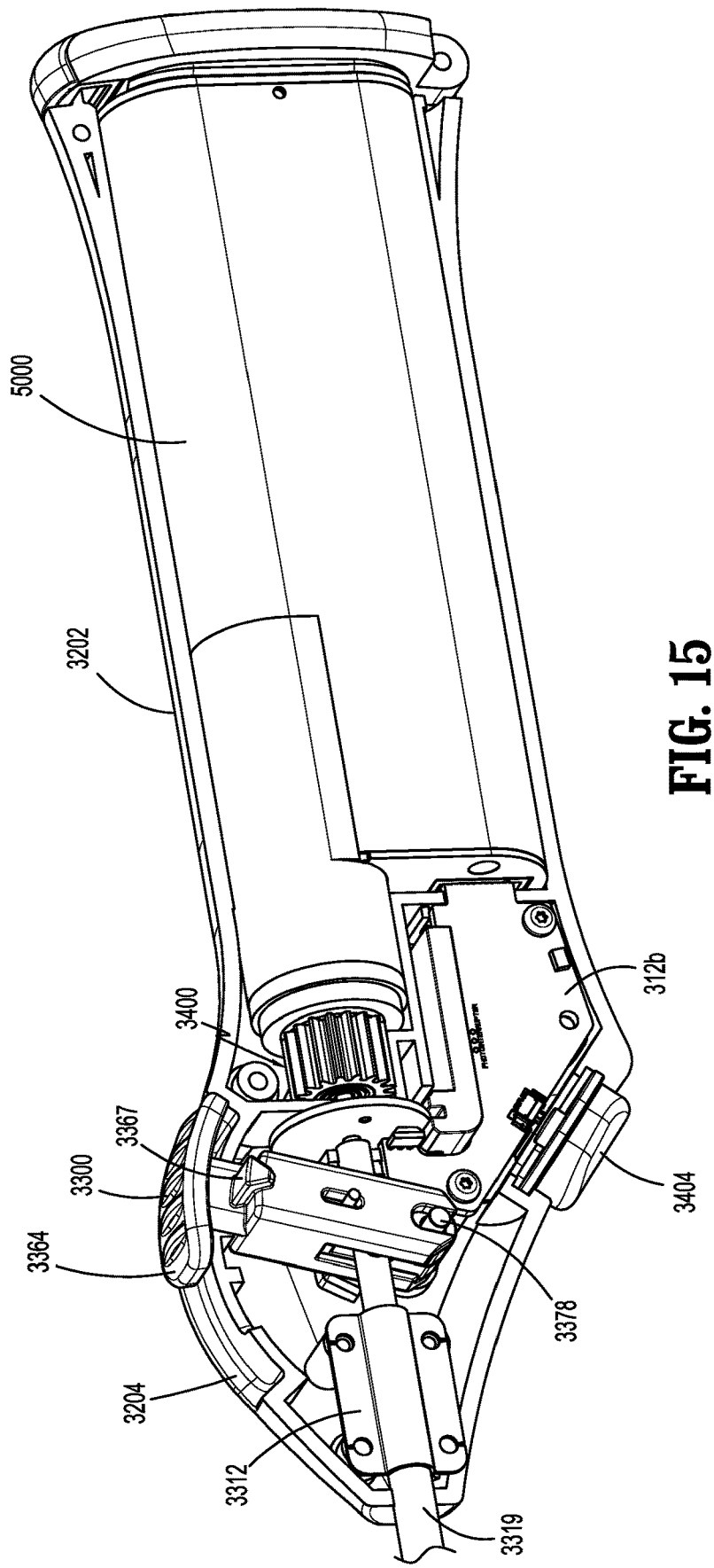
FIG. 15 is a partial perspective view of a handle assembly of the powered surgical tack applier of FIG. 14 with a portion of a housing removed.
Figure 16:
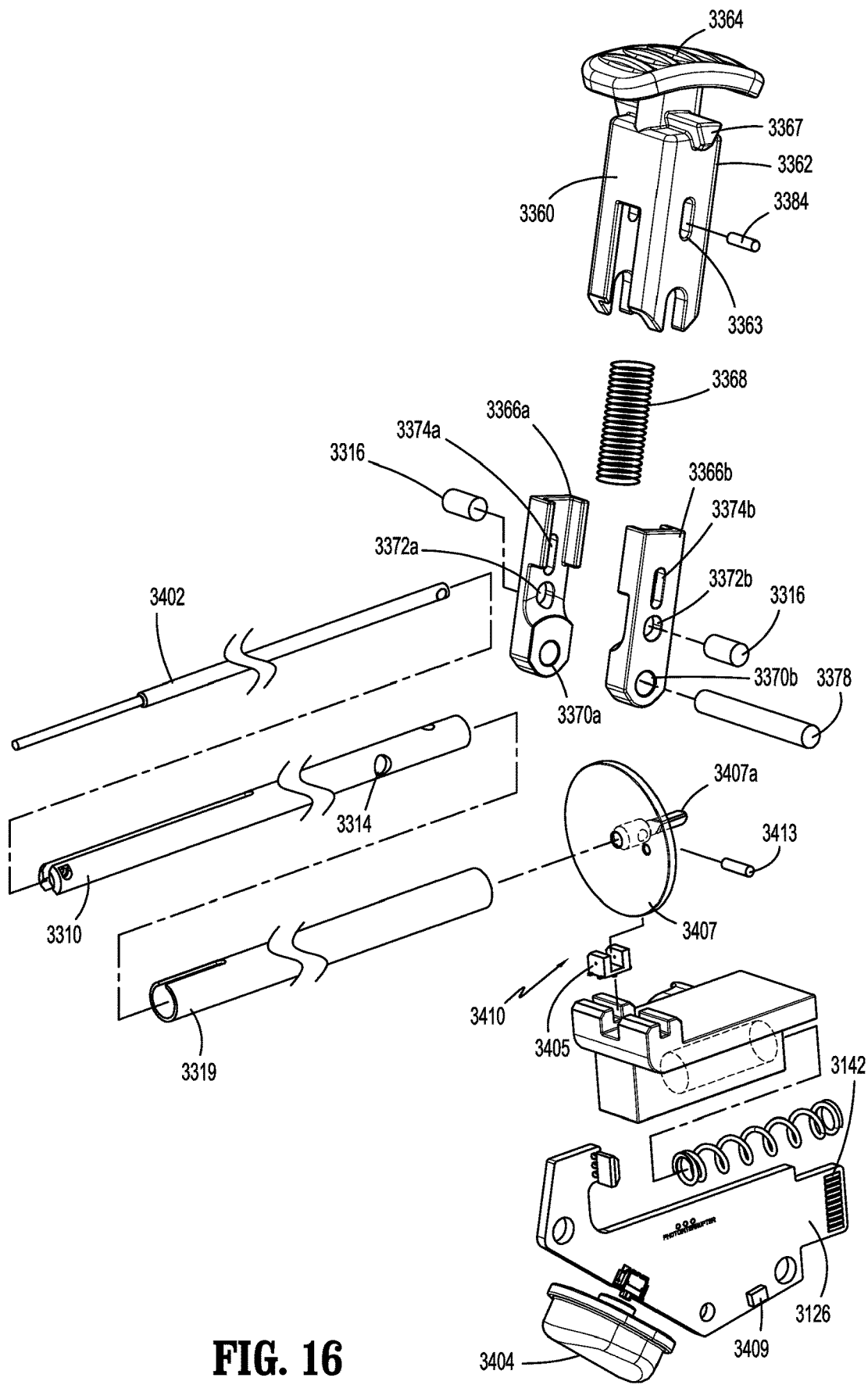
FIG. 16 is an exploded perspective view of an articulation assembly of the powered surgical tack applier of FIG. 14 with parts separated.

FIGS. 14-16 illustrate a powered surgical tack applier 3000 for applying the surgical tack 10 (FIG. 3) suitable for insertion through tissue "T" (FIG. 4) and the surgical mesh "M" (FIG. 5) in accordance with another aspect of the disclosure. The structural and functional features of the powered surgical tack applier 3000 that are substantially similar to those of the surgical tack applier described hereinabove will not described for the purposes of brevity, and as not to obscure the disclosure in unnecessary detail. The powered surgical tack applier 3000 includes a disposable portion and a resuable portion. The resuable portion includes a power module 5000 (FIG. 21) having a motor 5420 (FIG. 23), a battery 5440 (FIG. 23), and electronics, as will be discussed below. Under such a configuration, the powered surgical tack applier 3000 may aseptically receive the power module 5000. For example, a non-sterile power module 5000 may be received in a sealed compartment of the powered surgical tack applier 3000 such that the non-sterile power module 5000 is contained within a sealed barrier avoiding any potential contamination. The resuable power module 5000 may be compatible with various surgical device applications. For examples, other applications may include use in a linear tissue stapler, a circular stapler, and a small diameter stapler. A rechargeable battery has greater capacity than a disposable alternative, and a resuable motor may be of a higher quality and efficiency than would be possible in a fully disposable design. Ergonomics and user controls may be tailored to the particular application. Further, the power module 5000 enables stable control of the end effector with minimal movement on shaft and tissue. However, it is also contemplated that low-cost disposable power module may be permanently integrated into the handle assembly for a single use device.

FIG. 14 illustrates the powered surgical tack applier 3000 including a handle assembly 3200, an elongate member 3050 having an articulation portion 3060, and the loading unit 30 (FIG. 3) selectably connectable to a distal end of the elongate member 3050. The loading unit 30 is electromechanically coupled to the handle assembly 3200 and supports a plurality of surgical tacks 10. As the inner tube 38 of the loading unit 30 is rotated about a longitudinal axis "X-X" thereof, relative to the coil 36, the pair of tines $38b_1$ of the inner tube 38 transmits the rotation to the surgical tacks 10 and advance the surgical tacks 10 distally as the head threads 114a of the surgical tacks 10 engage with the coil 36.

FIG. 14 further illustrates the powered surgical tack applier 3000 including the articulation portion 3060 operatively coupled with an articulation lever assembly 3300 supported in the handle assembly 3200. As discussed hereinabove, the articulation portion 3060 may include a drive assembly having a slidable tube and an articulation arm pivotally coupled to the slidable tube. The articulation lever assembly 3300 is coupled to the slidable tube so that when the articulation lever assembly 3300 is actuated the slidable tube is displaced through the elongated member 3050. Longitudinal translation of the slidable tube moves the articulation arm to enable the loading unit 30 to articulate in a plane defined by the elongate member 3050 and the loading unit 30.

Figure 5:
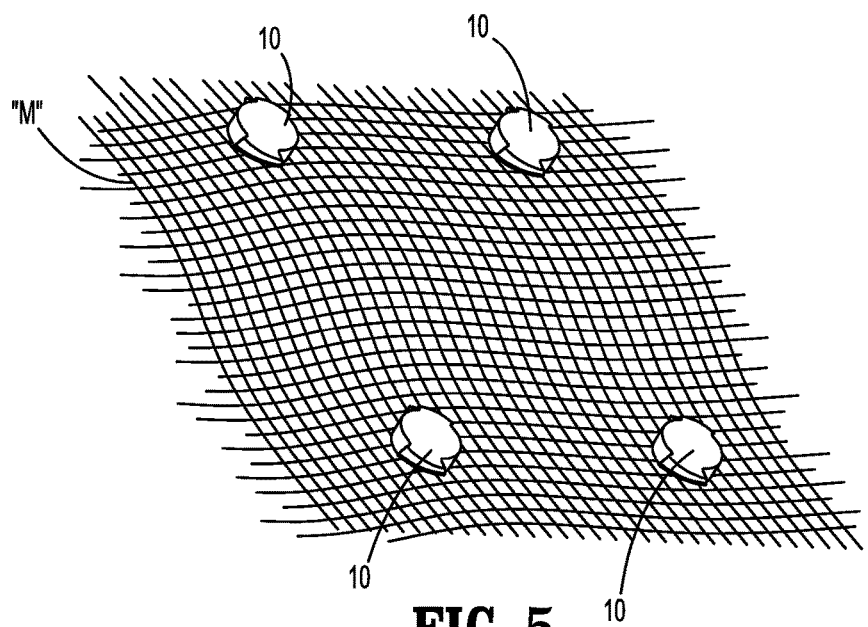
FIG. 5 is a perspective view of a surgical mesh for use with the powered surgical tack applier of FIG. 1, illustrating anchoring the surgical mesh to underlying tissue with a plurality of surgical tacks.

FIG. 15 illustrates the handle assembly 3200 including a housing 3202, the articulation lever assembly 3300 configured to articulate the articulation portion 3060 (FIG. 14) of the elongate member 3050, an actuation assembly 3400 configured to eject the surgical tack 10 (FIG. 3) out of the loading unit 30, and the power module 5000 removably secured to the housing 3202. The housing 3202 includes an ergonomic structure such that when the housing 3202 is gripped by a clinician, e.g., a thumb, may be positioned to slide the articulation lever assembly 3300 and, e.g., an index finger, may be positioned to trigger an actuation switch 3404 of the actuation assembly 3400. Actuation of the actuation assembly 3400 ejects a surgical tack 10 out of the loading unit 30 into body tissue "T" (FIG. 4) and through the mesh "M" (FIG. 5).

FIGS. 15 and 16 illustrate the articulation lever assembly 3300 including an articulation rod 3310 and articulation lever 3360 operatively coupled with the articulation rod 3310. The articulation rod 3310 is operatively coupled with the articulation portion 3060 of the elongate member 3050 of the powered surgical tack applier 3000. The articulation rod 3310 is slidable within an outer tube 3319 supported in the housing 3202 of the handle assembly 3200 by a mounting plate 3312. Axial displacement of the articulation rod 3310 causes articulation of the articulation portion 3060 based on the axial position of the articulation rod 3310. In particular, the articulation rod 3310 has an annular structure defining a channel dimensioned to receive the actuation rod 3402 of the actuation assembly 3400 therein. The articulation rod 3310 further defines a transverse bore 3314 dimensioned to receive articulation drive pins 3316 coupled with the articulation lever 3360.

FIG. 16 further illustrates the articulation lever 3360 including a housing portion 3362 and an engaging portion 3364 slidably engaging an engaging surface 3204 (FIG. 15) of the housing 3202. The engaging surface 3204 has an arcuate profile enabling the engaging portion 3364 to travel in, e.g., an arc. The housing portion 3362 is disposed within the housing 3202 and is dimensioned to receive articulation pivot arms 3366a, 3366b mated together to receive a biasing member 368 therebetween. Each articulation pivot arm 3366a, 3366b defines a first bore 3370a, 3370b, a second bore 3372a, 3372b, and a slot 3374a, 3374b. The first bores 3370a, 3370b are dimensioned to receive an articulation pivot pin 3378 pivotably coupling the articulation pivot arms 3366a, 3366b to the housing 3202. The second bores 3372a, 3372b are dimensioned to receive the respective articulation drive pins 3316 extending through the transverse bore 3314 of the articulation rod 3310. Under such a configuration, when the articulation pivot arms 3366a, 3366b are pivoted about the articulation pivot pin 3378, the articulation drive pins 3316 cause axial displacement of the articulation rod 3310. The actuation rod 3402 of the actuation assembly 3400 extends between the articulation drive pins 3316. The slots 3374a, 3374b of the articulation pivot arms 3366a, 3366b are dimensioned to cammingly receive a cam pin 3384 biased away from the articulation pivot pin 3378 by a biasing member 3368 interposed between the articulation pivot arms 3366a, 3366b.

The housing portion 3362 of the articulation lever 3360 is dimensioned to receive the mated articulation pivot arms 3366a, 3366b. The housing portion 3362 defines a slot 3363 dimensioned to cammingly receive the cam pin 3384 which is cammingly slidable in the slots 3374a, 3374b of the articulation pivot arms 3366a, 3366b. In addition, the housing portion 3362 includes a tooth 3367 configured to engage a detent portion 3208 (FIG. 18) of the housing 3202 to inhibit movement of the articulation lever 3360 relative to the housing 3202, thereby locking an axial position of the articulation rod 3310, which, in turn, locks the orientation of the articulation portion 3060 (FIG. 14) of the powered surgical tack applier 3000. Under such a configuration, the articulation lever 3360 is biased away from the articulation pivot pin 3378 such that the tooth 3367 of the housing portion 3362 engages the detent portion 3208. When the engaging portion 3364 of the articulation lever 3360 is depressed towards the housing 3202, the tooth 3367 is moved away from the detent portion 3208 enabling the clinician to slidably move the engaging portion 3364 on the engaging surface 3204 of the housing 3202, thereby enabling articulation of the articulation portion 3060 of the powered surgical tack applier 3000 to a desired orientation.

Figure 17:
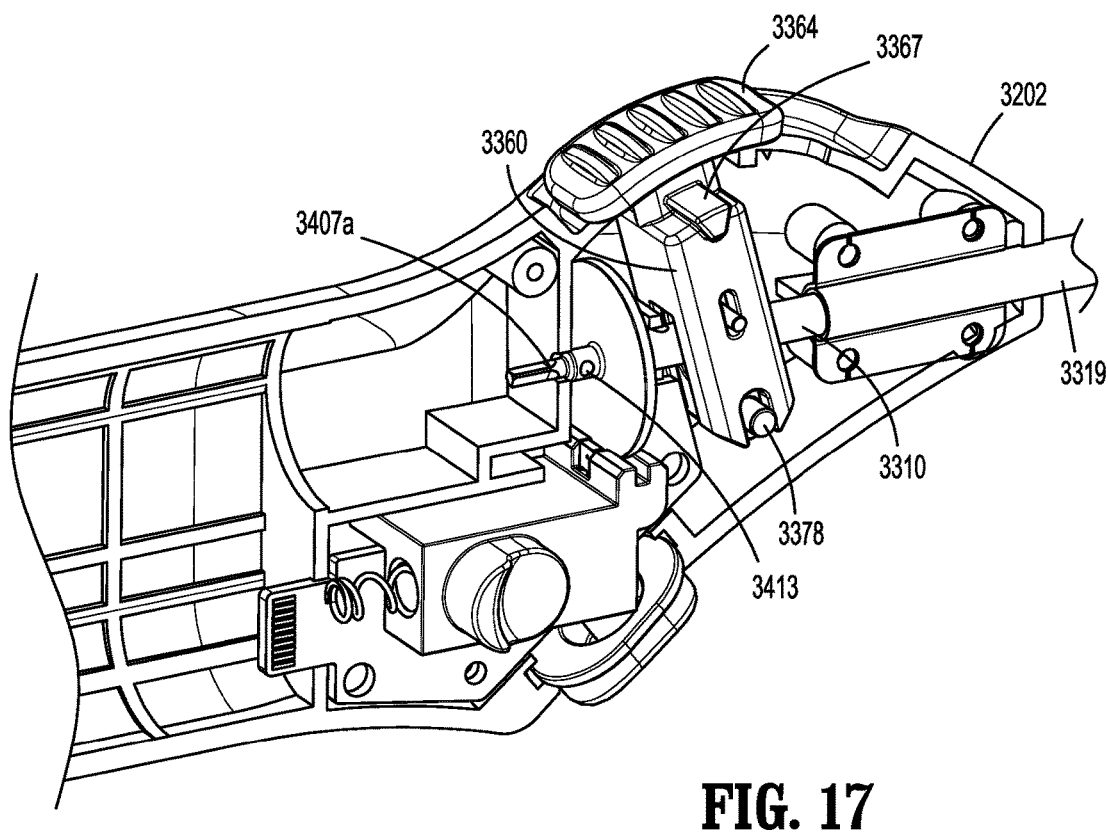
FIG. 17 is a partial perspective view of the handle assembly of FIG. 14.
Figure 18:
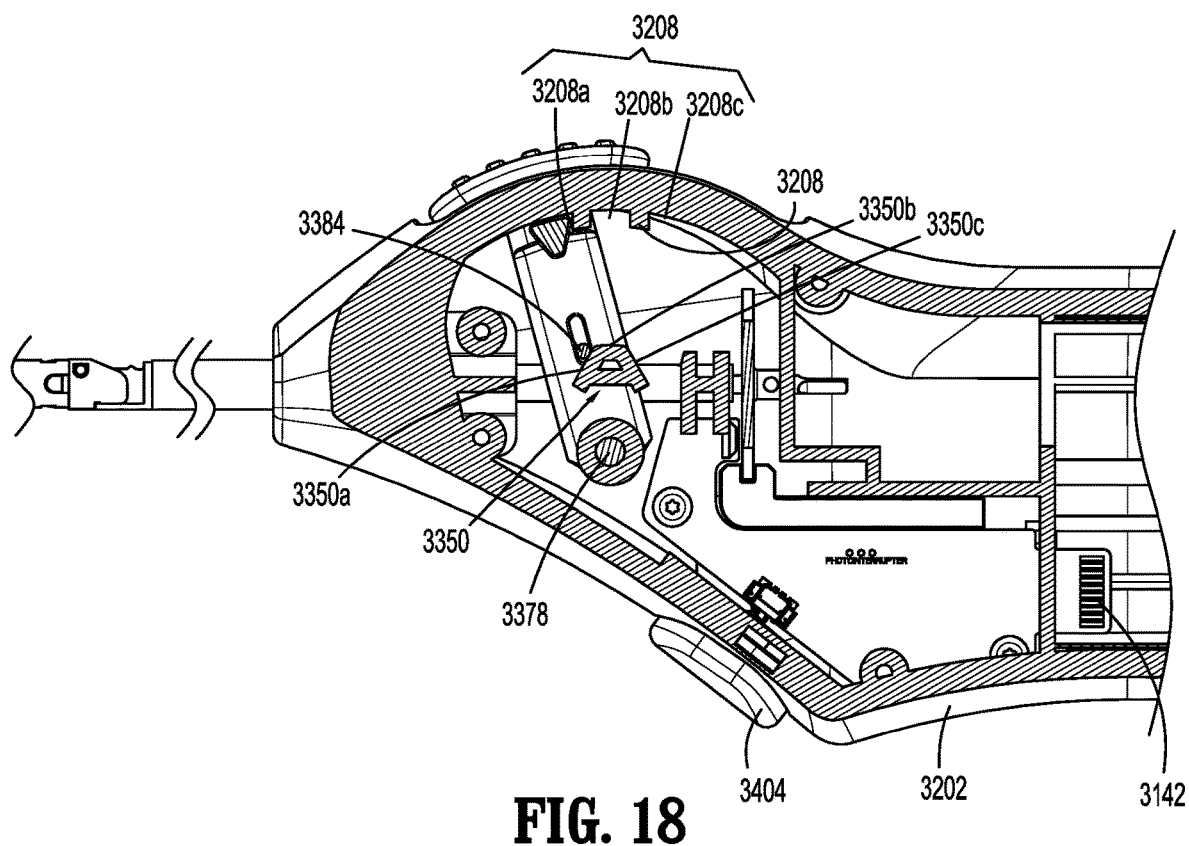
FIG. 18 is a cross-sectional view of the handle assembly of FIG. 14 taken along section line 18-18 of FIG. 14.
Figure 19:
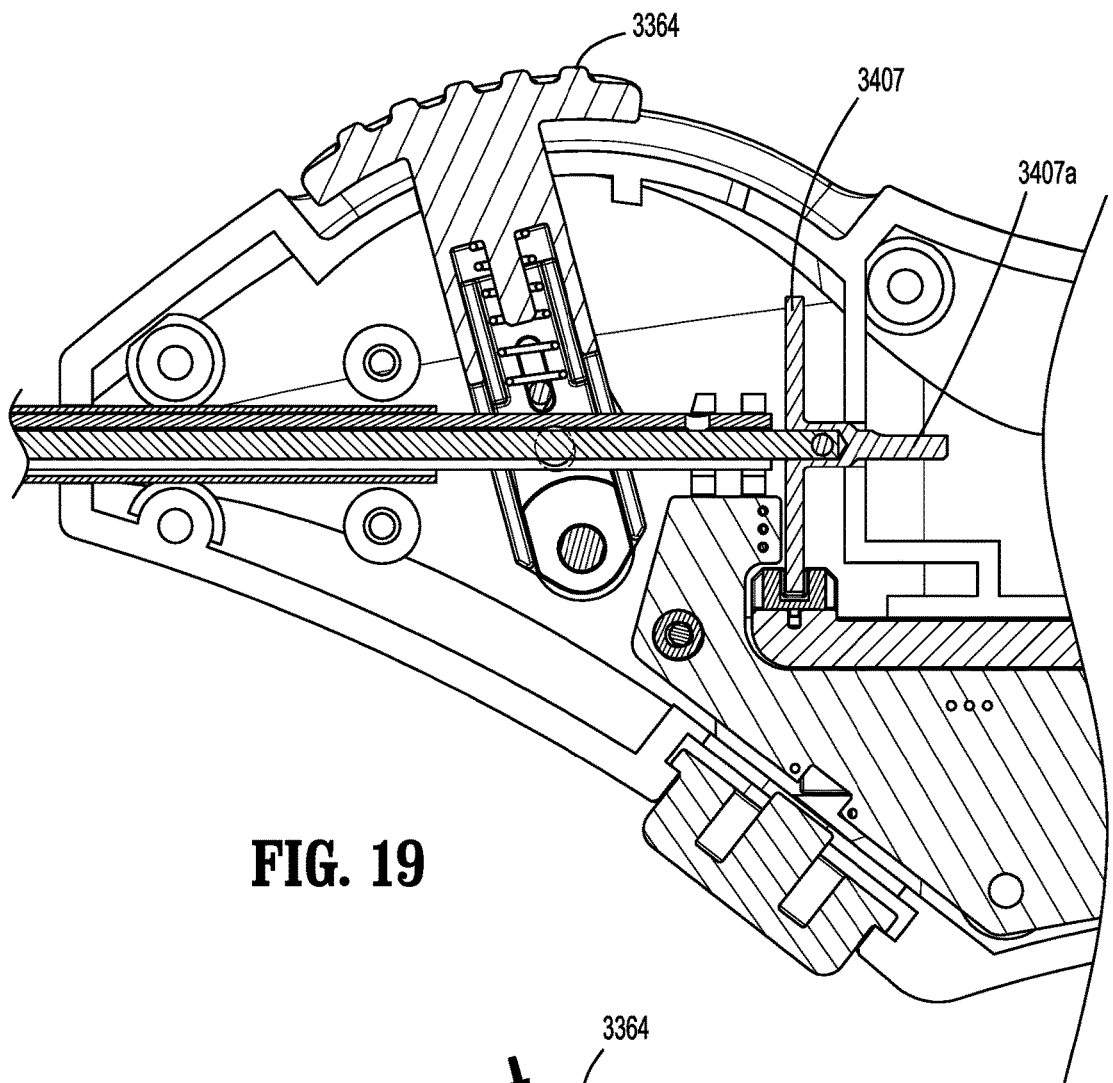
FIG. 19 is a cross-sectional view of the handle assembly of FIG. 14 taken along section line 19-19 of FIG. 14.

FIGS. 17 and 18 illustrate the articulation lever assembly 3300 further including a cam wedge 3350 having first, second, and third portions 3350a, 3350b, 3350c configured to cammingly engage the cam pin 3384 which is cammingly slidable in the slots 3374a, 3374b of the articulation pivot arms 3366a, 3366b and the slot 3363 of the articulation lever 3360. The first, second, and third portions 3350a, 3350b, 3350c correspond to the respective detent sections 3208a, 3208b, 3208c of the detent portion 3208. In this manner, articulation backlash is reduced as the cam pin 3384 rides along the first, second, and third portions 3350a, 3350b, 3350c of the cam wedge 3350.

FIGS. 15 and 16 illustrate the actuation assembly 3400 including an actuation rod 3402 operatively coupled with the loading unit 30 (FIG. 14), the power module 5000, an actuation switch 3404 configured to actuate a motor 5420 (FIG. 23) of the power module 5000 to eject the surgical tacks 10 from the loading unit 30, a printed circuit board 3126 including a microprocessor to control the actuation assembly 3400, and a battery 5440 (FIG. 23) of the power module 5000 electrically connected to the motor 3420 and the printed circuit board 3126. A proximal end of the actuation rod 3402 is operatively coupled with an output shaft 5421 (FIG. 25) of the motor 5420 such that when the actuation switch 3404 is triggered by the clinician, the motor 5420 is actuated to impart axial rotation to the actuation rod 5402, as will be discussed below. A distal end of the actuation rod 3402 is operatively coupled with the inner tube 38 (FIG. 3) of the loading unit 30 for concomitant rotation therewith.

The actuation assembly 3400 includes an encoder assembly 3410 operatively connected to the actuation rod 3402 and the processor of the printed circuit board 3126. The encoder assembly 3410 may include, e.g., an optical, motor encoder 3405 configured to keep an accurate count of turns of the rotational output shaft 5421 (FIG. 25) of the motor 5420 or the actuation rod 3402 to ensure a proper number of turns are made to insert the surgical tack 10 into, e.g., tissue "T" (FIG. 4) and the mesh "M" (FIG. 5). In addition, the encoder assembly 3410 may further include, e.g., an encoder wheel 3407, configured to ensure accurate clocking of a distal end of the actuation rod 3402 relative to the loading unit 30 (FIG. 14). For example, the encoder wheel 3407 may include a magnet thereon and the encoder assembly 3410 may include a Hall effect sensor. The encoder wheel 3407 may be concentrically coupled to the actuation rod 3402 by a pin 3413 for concomitant rotation. The encoder wheel 3407 further includes a protuberance 3407*a* (FIG. 17) configured to operatively engage the power module 5000, as will be described below. The encoder assembly 3410 may further include a light emitting diode ("LED") indicator 3409 to indicate status of the ejection of each surgical tack 10. For example, a green light may indicate proper application of the surgical tact 10 through the mesh "M" and into tissue "T", and a red light may indicate, e.g., improper application of the surgical tack 10, due to an error signal from the optical motor encoder 3405 or the single notched encoder wheel 3407. Alternatively, the encoder assembly 3410 may further include a piezoelectric element for providing an audible tone for proper application of the surgical tack 10.

Figure 21:
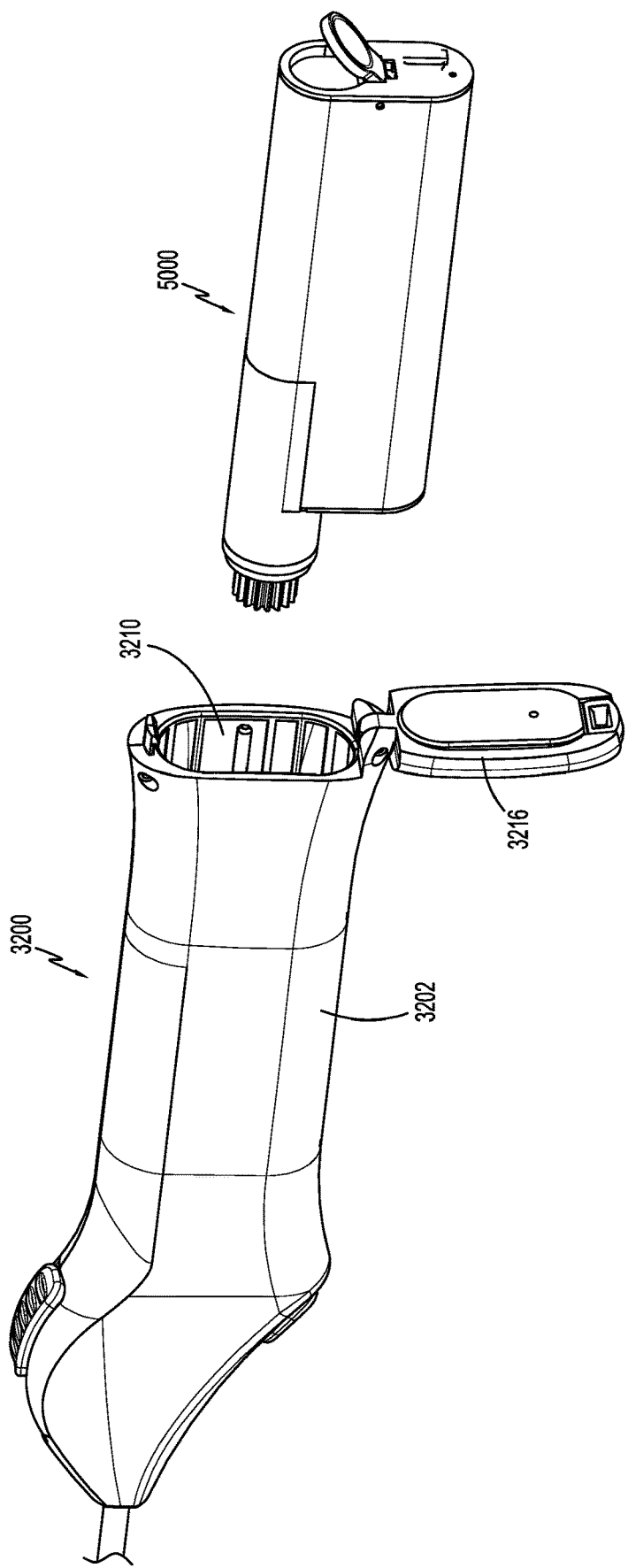
FIG. 21 is a perspective view of the handle assembly of FIG. 14 with a power module separated therefrom.
Figure 22:
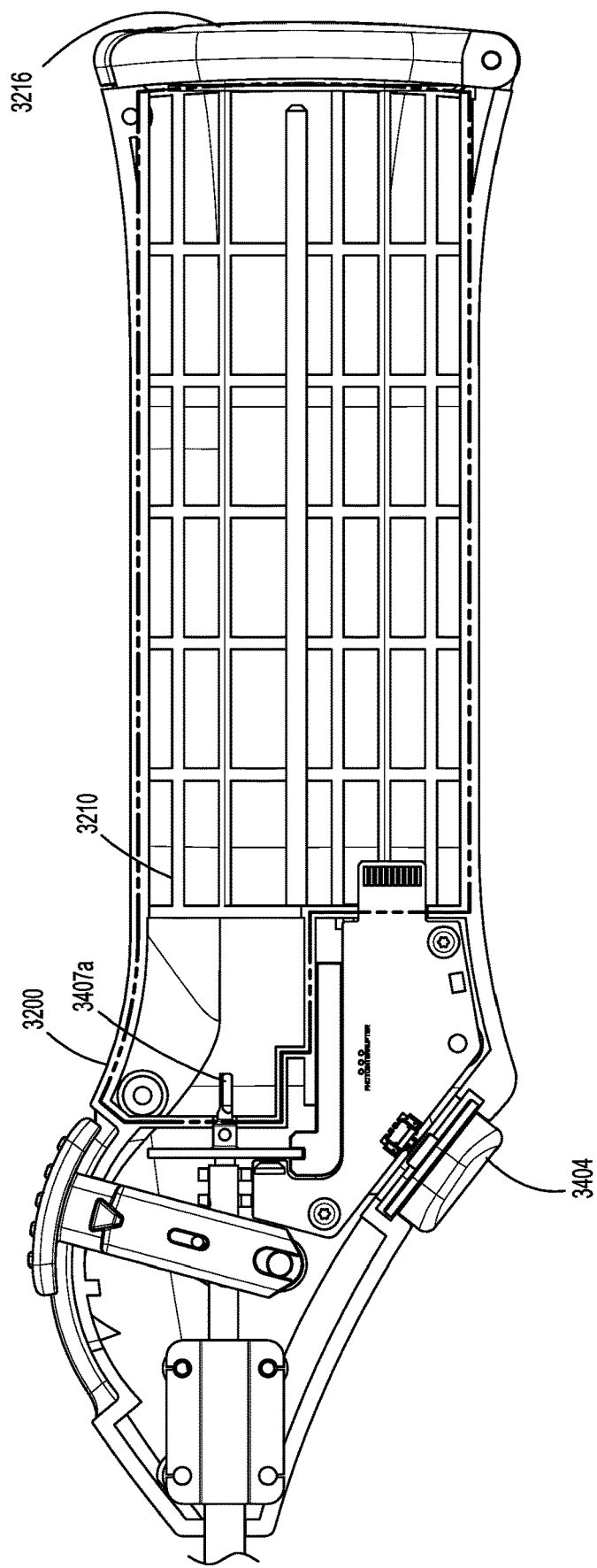
FIG. 22 is a cross-sectional view of the handle assembly of FIG. 14 with the power module removed therefrom.

FIGS. 21 and 22 illustrate the handle assembly 3200 defining a chamber 3210 configured to removably receive the power module 5000 therein. The chamber 3210 provides a seal to hermetically seal the chamber 3210. The power module 5000 may be reusable and is configured to operate various functions of different types of surgical end effectors, such as, for example, the powered surgical tack applier 3000, a linear stapler, a circular stapler, and a small-diameter vascular stapler. The power module 5000 has two outputs with each operably coupled to the same motor of the power module. The outputs are rotated simultaneously by the motor, but each at a different speed and torque from the other. A high-speed/low-torque output may be disposed concentrically within a high-torque/low-speed output. Depending on the surgical instrument in which the power module is received and operably engaged with, either the high-speed/low-torque output or the high-torque/low-speed output of the power module selectively engages a corresponding driven component (e.g., a rod, screw, rack, gear, or the like) of the selected surgical instrument. As such, the same power module may be used in a variety of surgical instruments despite each of the surgical instruments having discrete power and speed requirements.

Figure 23:
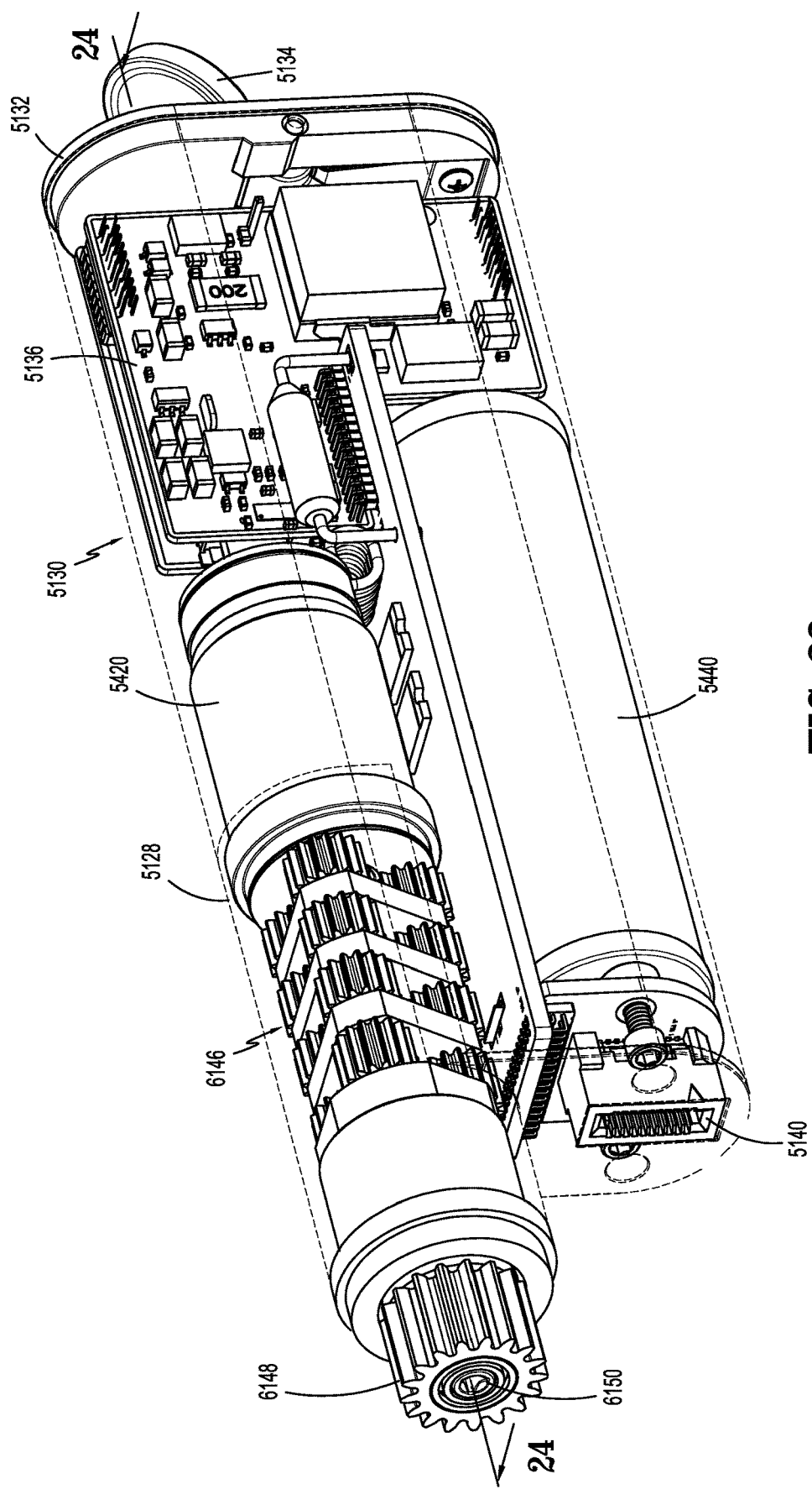
FIG. 23 is a perspective view of the power module of FIG. 21.

The handle assembly 3200 includes a disposable and sterile housing 3202. A door 3216 is pivotably coupled to the housing 3202. The door 3216 is selectively opened and closed to allow for the placement or removal of a non-sterile or sterile power module 5000. FIG. 23 illustrates the power module 5000 including a sterile outer shell 5128 (shown in phantom) and a reusable power assembly 5130 for removable receipt in the outer shell 5128. The outer shell 5128 has a cover 5132 received in an open proximal end of the outer shell 5128, and a spring-loaded pull tab 5134 to facilitate removal of the cover 5132.

Figure 20:
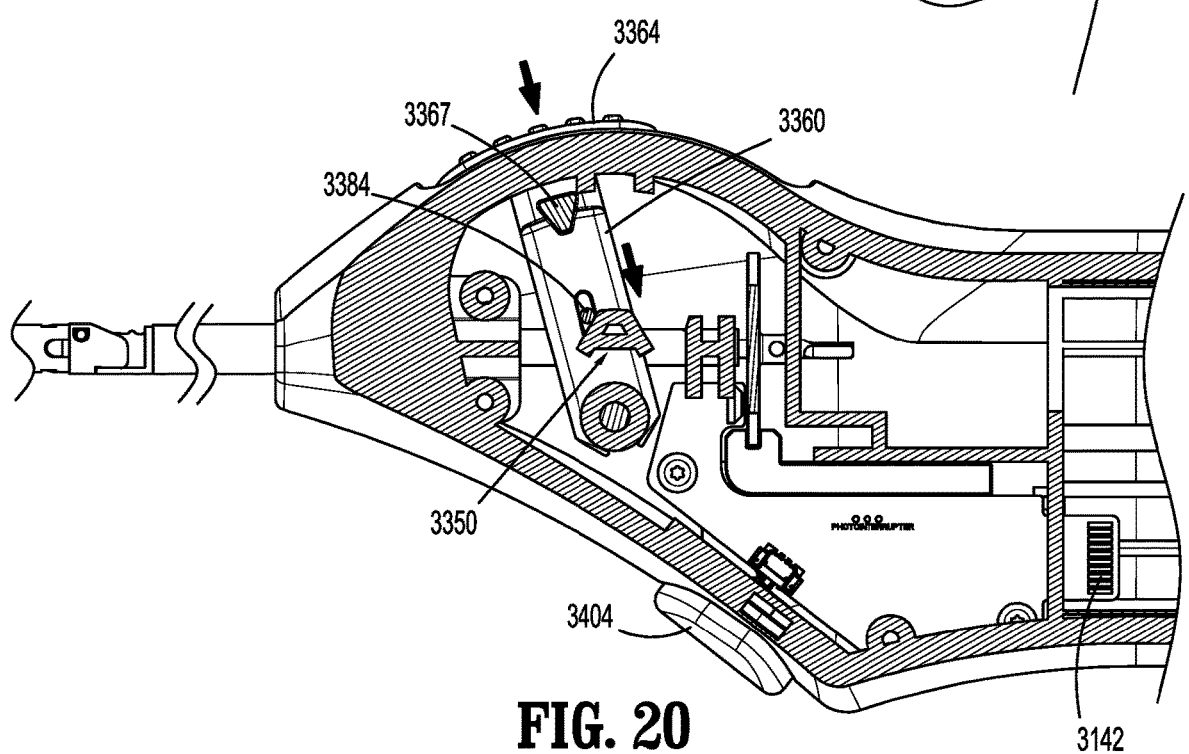
FIG. 20 is a cross-sectional view of the handle assembly of FIG. 19 illustrating use thereof.

FIG. 23 illustrates the power assembly 5130 including the motor 5420, such as, for example, an electrical drive motor, which is electrically connected or wirelessly connected to a printed circuit board 5136 and the battery 5440. In aspects, the battery 5440 may include a boost circuit and may be rechargeable (e.g., wirelessly). The battery 5440 has a card edge connector 5140 configured for detachable receipt of a card edge header 3142 (FIG. 20) of the handle assembly 3200 to enable communication between the actuation switch 3404 and the battery 5440. The printed circuit board 5136 may include a USB charging connector to enable charging of the battery 5440 to be recharged with a USB charger or wirelessly (e.g., via induction). In aspects, the printed circuit board 5136 may have a motor controller or a processor. By providing a reusable power module 5000, the battery 5440 may be a rechargeable single cell with a boost circuit to provide the necessary voltage. A rechargeable battery has greater capacity than a disposable alternative. Further, the motor 5420 may be of a higher quality and higher efficiency than would be possible in a fully disposable design.

Figure 24:
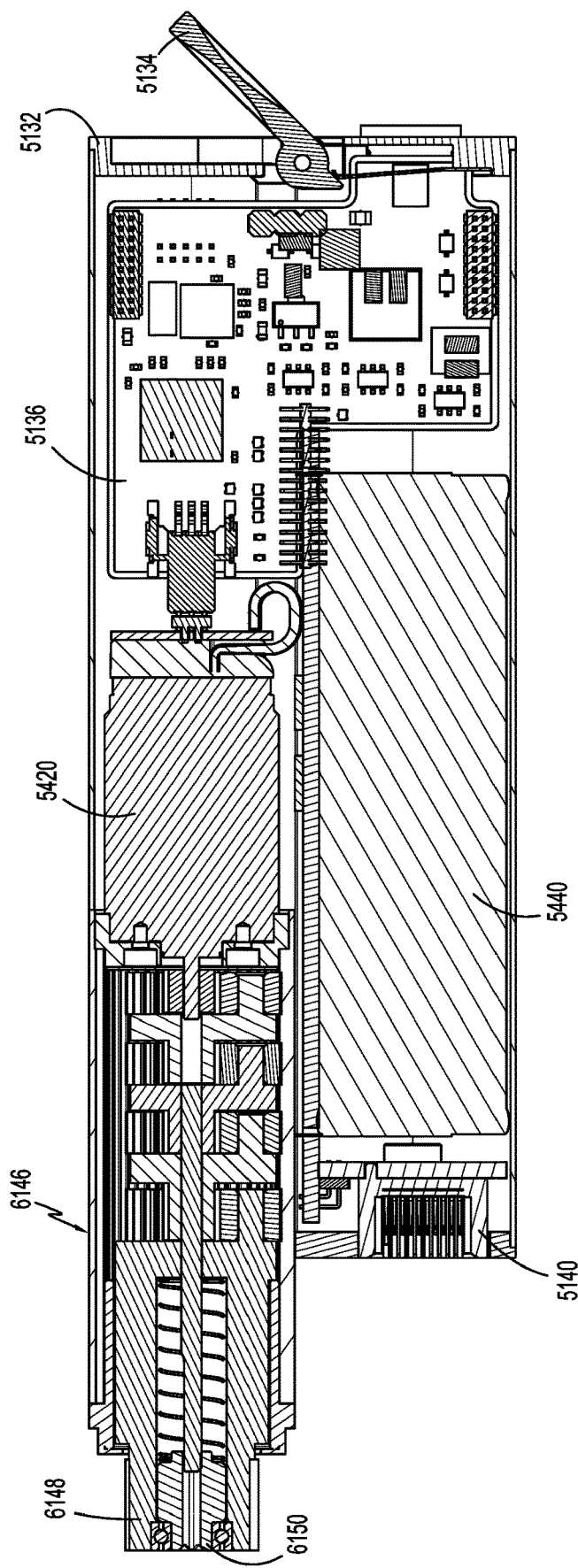
FIG. 24 is a cross-sectional view of the power module of FIG. 23.
Figure 25:
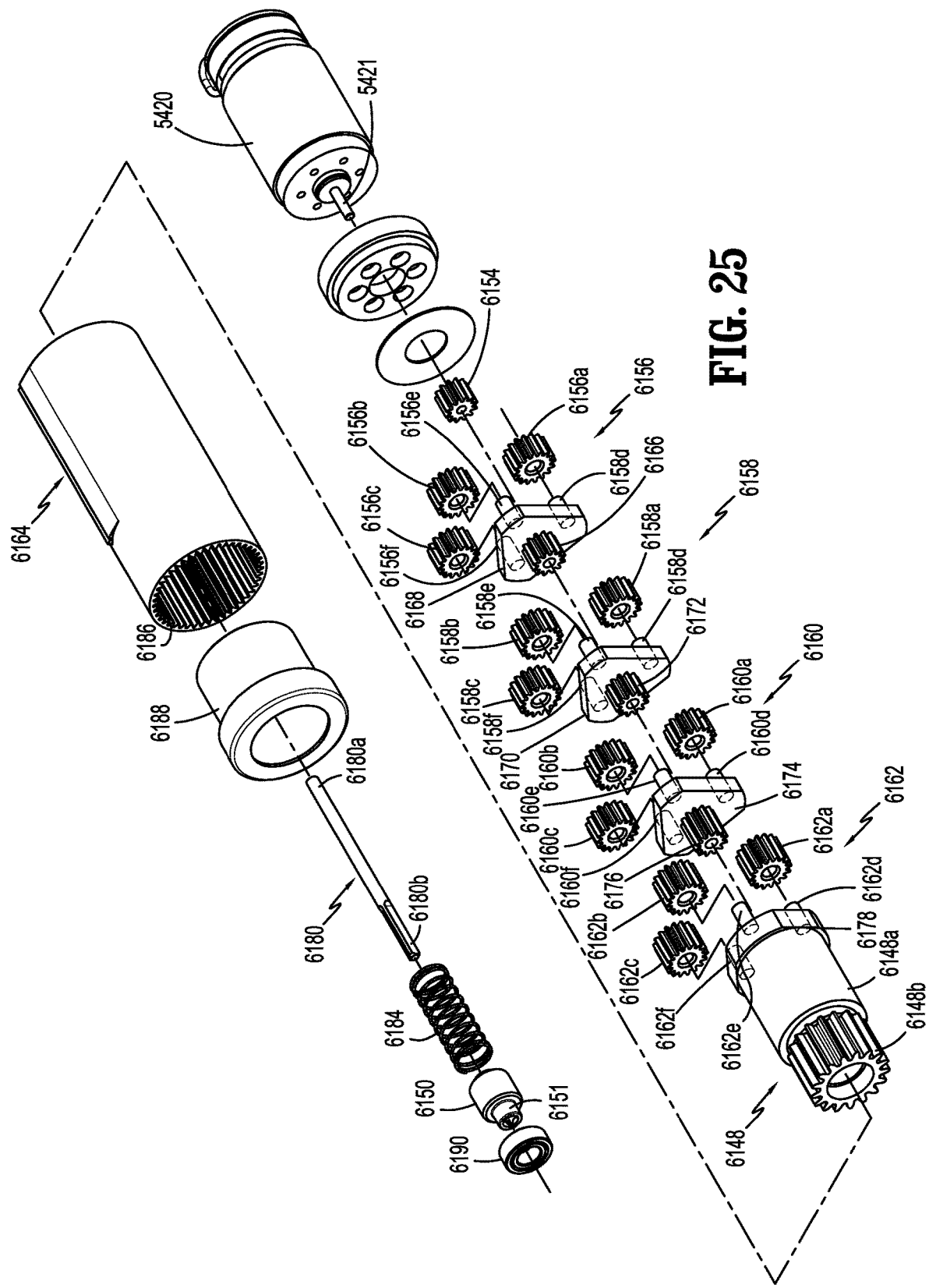
FIG. 25 is an exploded perspective view of a gear box of the power module of FIG. 21 with parts separated.

FIGS. 24 and 25 illustrate the power module 5000 further including a gearbox 6146 such as, for example, a planetary gearbox, operably coupled to the motor 5420, and first and second outputs 6148, 6150 and configured to rotate about a longitudinal axis defined by the gearbox 6146. The gear box 6146 is configured to transfer power from the motor 5420 to a rotational output of the first output 6148 at a high-torque and low-speed, and a rotational output of the second output 6150 at a high-speed and low-torque. Rotation of the first and second outputs 6148, 6150 may be utilized to perform the operation of end effectors of surgical instruments. In particular, the high-speed/low torque rotation of the second output 6150 is utilized to effect rotation of the actuation rod 3402.

FIG. 25 illustrates the motor 5420 having an output shaft 5421 to which a main sun gear 154 is fixed such that the main sun gear 6154 rotates concomitantly with the output shaft 5421. The gear box 6146 includes a plurality of planetary gear assemblies 6156, 6158, 6160, 6162 and an elongate ring gear 6164 operably engaging the plurality of planetary gear assemblies 6156, 6158, 6160, 6162.

The first planetary gear assembly 6156 is operably coupled to the main sun gear 6154 such that the first planetary gear assembly 6156 rotates about a longitudinal axis of the output shaft 5421 of the motor 5420 in response to rotation of the main sun gear 6154. The first planetary gear assembly 6156 increases the torque output of the motor 5420 while reducing the output rotational speed. The first planetary gear assembly 6156 includes a first carrier 6168, a first sun gear 6166, and a plurality of planetary gears 6156*a*, 6156*b*, 6156*c*. The first carrier 6168 has a plurality (e.g., three) of pins 6156*d*, 6156*e*, 6156*f* fixed thereto and extending proximally from a proximal side thereof. The first sun gear 6166 is rotationally fixed to a distal side of the first carrier 6168 and centrally aligned with the longitudinal axis of the output shaft 5421. The planetary gears 6156*a*, 6156*b*, 6156*c* are rotatably coupled to the respective pins 6156*d*, 6156*e*, 6156*f* of the first carrier 6168. The planetary gears 6156*a*, 6156*b*, 6156*c* are in meshing engagement with the main sun gear 6154 to rotate in response to rotation of the main sun gear 6154. As will be described, the elongate ring gear 6164 is rotationally fixed relative to the outer shell 5128 (FIG. 20) such that the first planetary gear assembly 6156 rotates as a unit about the longitudinally axis of the output shaft 5421 of the motor 5420 in response to a rotation of the main sun gear 6154.

The second planetary gear assembly 6158 includes a second carrier 6170, a second sun gear 6172, and a plurality of planetary gears 6158*a*, 6158*b*, 6158*c*. The second planetary gear assembly 6158 has an increased torque output and reduced rotational speed output relative to the first planetary gear assembly 6156. The second carrier 6170 has a plurality (e.g., three) of pins 6158*d*, 6158*e*, 6158*f* fixed thereto and extending proximally from a proximal side thereof. The second sun gear 6172 is rotationally fixed to a distal side of the second carrier 6170 and centrally aligned with the longitudinal axis of the output shaft 5421 of the motor 5420. The planetary gears 6158a, 6158b, 6158c of the second planetary gear assembly 6158 are rotatably coupled to the respective pins 6158d, 6158e, 6158f of the second carrier 6170. The planetary gears 6158a, 6158b, 6158c are in meshing engagement with the first sun gear 6166 of the first planetary gear assembly 6156 and the fixed elongate ring gear 6164 such that the second planetary gear assembly 6158 rotates in response to rotation of the first planetary gear assembly 6156.

The third planetary gear assembly 6160 includes a third carrier 6174, a third sun gear 6176, and a plurality of planetary gears 6160a, 6160b, 6160c. The third planetary gear assembly 6160 has an increased torque output and reduced rotational speed output relative to the second planetary gear assembly 6158. The third carrier 6174 has a plurality (e.g., three) of pins 6160d, 6160e, 6160f fixed thereto and extending proximally from a proximal side thereof. The third sun gear 6176 is rotationally fixed to a distal side of the third carrier 6174 and centrally aligned with the longitudinal axis of the output shaft 5421 of the motor 5420. The planetary gears 6160a, 6160b, 6160c of the third planetary gear assembly 6160 are rotatably coupled to the respective pins 6160d, 6160e, 6160f of the third carrier 6174. The planetary gears 6160a, 6160b, 6160c of the third planetary gear assembly 6160 are in meshing engagement with the second sun gear 6172 of the second planetary gear assembly 6158 and the elongate ring gear 6164 such that the third planetary gear assembly 6160 rotates as a unit in response to a rotation of the second planetary gear assembly 6158.

The fourth planetary gear assembly 6162 includes a fourth carrier 6178 and a plurality of planetary gears 6162a, 6162b, 6162c. The fourth planetary gear assembly 6162 has an increased torque output and reduced rotational speed output relative to the third planetary gear assembly 6160. The fourth carrier 6178 is connected to, monolithically formed with, or otherwise non-rotatably coupled to a proximal end of the first output 6148 and has a plurality (e.g., three) of pins 6162d, 6162e, 6162f fixed thereto and extending proximally from a proximal side thereof. The planetary gears 6162a, 6162b, 6162c of the fourth planetary gear assembly 6162 are rotatably coupled to the respective pins 6162d, 6162e, 6162f of the fourth carrier 6178. The planetary gears 6162a, 6162b, 6162c of the fourth planetary gear assembly 6162 are in meshing engagement with the third sun gear 6176 of the third planetary gear assembly 6160 and the elongate ring gear 6164 such that the fourth planetary gear assembly 6162 and the first output 6148 rotate together in response to rotation of the third planetary gear assembly 6160. It is contemplated that the gear box 6146 may include more or less than the four planetary gear assemblies and/or other types of gears.

The first output 6148 is configured to generate a relatively high torque (e.g., about 625 oz-in) and a relatively low speed (e.g., 24 rpm) and includes a cylindrical body 6148a received in a distal end portion of the elongate ring gear 6164, and a gear 6148b, such as, for example, a pinion gear formed with a distal end portion of the cylindrical body 6148a. The pinion gear 6148b of the first output 6148 is configured to be selectively operably coupled to a driven member of a first type of surgical end effector, such as, for example, surgical end effector 20. It is contemplated that a handle assembly may have a corresponding driven component (e.g., a gear, rack, or the like) configured to selectively engage the pinion gear 6148b upon receipt of the power module 5000 in the handle assembly 3200.

The power module 5000 further includes a drive shaft 6180 having a proximal end portion 6180a non-rotatably coupled to the second planetary gear assembly 6158 such that the drive shaft 6180 is configured to rotate with the second planetary gear assembly 6158. In particular, the proximal end portion 6180a of the drive shaft 6180 is received within and rotationally fixed to the second sun gear 6172 of the second planetary gear assembly 6158. The drive shaft 6180 has a distal end portion 6180b extending longitudinally through the third and fourth planetary gear assemblies 6160, 6162 while being freely rotatable therein. The distal end portion 6180b of the drive shaft 6180 may have a non-circular cross-sectional shape, such as, for example, a tri-lobe shape.

The second output 6150 is attached to the distal end portion 6180b of the drive shaft 6180 and is configured to rotate with the drive shaft 6180 about a longitudinal axis of the drive shaft 6180. The second output 6150 is configured to generate a relatively low torque (e.g., 25 oz-in) and a relatively high speed (e.g., 600 rpm) and includes a socket 6151 that is configured to operably couple to a corresponding driven element of a different type of surgical end effector than the first output 6148. The powered surgical tack applier 3000 demands less torque but higher actuation speed than other surgical instruments such as, e.g., a linear stapler. When the power module 5000 is inserted into the chamber 3210 of the handle assembly 3200, the socket 6151 of the second output 6150 engages a driven element, i.e., the protuberance 3407a (FIG. 16) of encoder wheel 3407, to provide rotation to the actuation rod 3402 (FIG. 16). It is contemplated that the handle assemblies or other components of the surgical instruments have a corresponding driven component (e.g., a rod) configured to selectively engage the socket 6151 upon receipt of the power module 5000 in the handle housing.

The second output 6150 is concentrically disposed within the first output 6148 and is configured to rotate simultaneously with the first output 6148 in response to an activation of the same motor, namely the motor 5420. However, as noted above, the first and second outputs 6148, 6150 rotate at different speeds and with different torques from one another. The second output 6150 is received in an elongate cavity 6182 defined in the cylindrical body 6148a of the first output 6148. A biasing member 6184 is disposed within the cavity 6182 and captured between the second output 6150 and an inner surface of the cylindrical body 6148a of the first output 6148. The biasing member 6184 is configured to distally-bias the second output 6150 into a position in which the second output 6150 is concentric within the first output 6148.

The elongate ring gear 6164 of the gear box 6146 encapsulates each of the planetary gear assemblies 6156, 6158, 6160, 6162 and is rotationally fixed relative to the sterile outer shell 5128 (FIG. 23) and the motor 5420. The elongate ring gear 6164 has an annular inner surface defining a plurality of longitudinally-extending teeth 6186 that are in meshing engagement with the planetary gears of each of the planetary gear assemblies 6156, 6158, 6160, 6162. A first bushing 6188 may be provided to capture the first output 6148 in the elongate ring gear 6164 and a second bushing 6190 may be provided to capture the second output 6150 in the first output 6148.

In use, the loading unit 30 is operatively mounted to a distal end of the elongate member 3050. The power module 5000 is inserted into the handle housing 3200, whereby the protuberance 3407a (FIG. 16) of the encoder wheel 3407 engages the socket 6151 (FIG. 25) of the second output 6050. With the power module 5000 disposed within the handle housing 3200, the door 3216 is closed, thereby sealing the power module 5000 in the chamber 3210. Further, the card edge header 3142 (FIG. 16) of the printed circuit board 3126 of the handle assembly 3200 is connected to the card edge connector 5140 (FIG. 24) of the power module 5000. The loading unit 30 is introduced into a target surgical site while in the non-articulated condition. The clinician may remotely articulate loading unit 30 to access the surgical site. Specifically, the clinician may slide the engaging portion 3364 (FIG. 16) of the articulation lever 3360 along the engaging surface 3204 of the housing 3202. As the articulation rod 3310 is displaced axially, the loading unit 30 is moved to an articulated orientation relative to the central longitudinal axis "X-X". Furthermore, the clinician may position the surgical mesh "M" adjacent the surgical site. Once the surgical mesh "M" is properly positioned on the surgical site, the clinician may trigger the actuation switch 3404 to eject a surgical tack 10 through the mesh "M" and into tissue "T". To deploy the surgical tacks 10, the actuation switch 3404 may be toggled, whereby the battery 5440 of the power module 5000 supplies power to the motor 5420, which drives a rotation, in turn, of the first and second planetary gear assemblies 6156, 6158. Since the drive shaft 6180 is fixed to the second sun gear 6172 of the second planetary gear assembly 6158, the drive shaft 6180 rotates with the rotation of the second planetary gear assembly 6158. The second output 6150, which is non-rotatably attached to the distal end portion 6180b of the drive shaft 6180, rotates with the drive shaft 6180 to deploy the surgical tack 10 into tissue at a low torque and a high speed.

While various configurations have been shown in the drawings, it is not intended that the disclosure be limited thereto, as it is intended that the disclosure be as broad in scope as the art will allow and that the specification be read likewise. In aspects, a proximal end portion or any suitable location of the housing 3202 may have a clear window to allow for viewing of a display (e.g., an LCD, not shown). In addition, the first and second drive outputs 6148, 6150 may be simultaneously coupled to two distinct driven elements of a particular surgical instrument to perform discrete functions of the surgical instrument. Any of the gears disclosed herein may be configured as any suitable gear, such as bevel gears, spur gears, spiral gears, worm gears, or the like. It is also contemplated that the first output 6148 may be utilized for high-torque, low-speed output requirement such as, e.g., articulation of the articulation portion 3060. Therefore, the above description should not be construed as limiting, but merely as exemplifications. Those skilled in the art will envision other modifications within the scope and spirit of the claims appended hereto.

The invention claimed is:
1. A powered surgical tack applier comprising:
a handle assembly including:
an actuation assembly including an actuation rod and an actuation switch; and
an articulation lever assembly including an articulation rod and an articulation lever operatively coupled with the articulation rod;
an elongate member extending distally from the handle assembly, the elongate member including:
a loading unit having a plurality of surgical tacks, the loading unit operatively coupled to the actuation rod of the actuation assembly such that rotation of the actuation rod deploys a surgical tack of the plurality of surgical tacks from the loading unit; and
an articulation portion pivotable with respect to a longitudinal axis defined by the elongate member, the articulation portion being operatively coupled to the articulation rod of the handle assembly such that axial displacement of the articulation rod articulates the articulation portion; and
a power module removably received in the handle assembly, the power module including:
a motor operatively coupled to the actuation rod of the actuation assembly to rotate the actuation rod;
a battery electrically coupled to the motor to supply power to the motor; and
a gear box including:
a main sun gear fixed to an output shaft of the motor for concomitant rotation with the output shaft;
a first planetary gear assembly operably coupled to the main sun gear such that the first planetary gear assembly rotates about a longitudinal axis defined by the output shaft in response to rotation of the main sun gear;
a second planetary gear assembly operably coupled to the first planetary gear assembly such that the second planetary gear assembly rotates in response to the rotation of the first planetary gear assembly;
a drive shaft coupled to the second planetary gear assembly such that the drive shaft rotates with the second planetary gear assembly;
a third planetary gear assembly operably coupled to the second planetary gear assembly such that the third planetary gear assembly rotates in response to the rotation of the second planetary gear assembly;
a fourth planetary gear assembly operably coupled to the third planetary gear assembly such that the fourth planetary gear assembly rotates in response to the rotation of the third planetary gear assembly; and
a high-speed output coupled to the drive shaft for concomitant rotation therewith, the high-speed output operably coupled to the actuation rod of the handle assembly.

2. The powered surgical tack applier according to claim 1, wherein the gear box of the power module further includes a high-torque output being non-rotatably coupled to the fourth planetary gear assembly such that the high-torque output rotates with the fourth planetary gear assembly.

3. The powered surgical tack applier according to claim 2, wherein the high-speed output is concentrically disposed within the high-torque output.

4. The powered surgical tack applier according to claim 2, wherein the high-speed and high-torque outputs are simultaneously rotatable in response to activation of the motor.

5. The powered surgical tack applier according to claim 2, wherein the drive shaft has a proximal end portion fixed to the second planetary gear assembly, and a distal end portion rotatable relative to the high-torque output within the high-torque output.

6. The powered surgical tack applier according to claim 2, wherein the high-torque output defines a cavity dimensioned to receive the high-speed output therein.

7. The powered surgical tack applier according to claim 1, wherein the drive shaft extends longitudinally through the third and fourth planetary gear assemblies.

8. The powered surgical tack applier according to claim 1, wherein the actuation assembly further includes a processor configured to control the motor.

9. The powered surgical tack applier according to claim 1, wherein the actuation assembly further includes an optical motor encoder configured to count number of turns of the output shaft of the motor to ensure a desired number of turns are made to insert a surgical tack into tissue, the optical motor encoder operatively connected to the actuation rod and the processor.

10. The powered surgical tack applier according to claim 9, wherein the actuation assembly further includes an encoder wheel configured to ensure correct clocking of a distal end of the actuation rod relative to the loading unit.

11. The powered surgical tack applier according to claim 1, wherein the gear box of the power module further includes an elongate ring gear in engagement with the first, second, third and fourth planetary gear assemblies.

12. The powered surgical tack applier according to claim 11, wherein the first, second, third, and fourth planetary gear assemblies are disposed within the elongate ring gear.

13. The powered surgical tack applier according to claim 11, wherein the elongate ring gear is rotationally fixed relative to the motor.

14. A powered surgical tack applier comprising:
a handle assembly including:
an actuation assembly including an actuation rod; and
an articulation lever assembly including an articulation rod and an articulation lever operatively coupled with the articulation rod;
an elongate member extending distally from the handle assembly, the elongate member including:
a loading unit having a plurality of surgical tacks, the loading unit operatively coupled to the actuation rod of the actuation assembly such that rotation of the actuation rod deploys a surgical tack of the plurality of surgical tacks from the loading unit; and
an articulation portion pivotable with respect to a longitudinal axis defined by the elongate member, the articulation portion being operatively coupled to the articulation rod of the handle assembly such that axial displacement of the articulation rod articulates the articulation portion;
a power module removably received in the handle assembly, the power module including:
a motor having an output shaft;
a main sun gear fixed to the output shaft and configured to rotate with the output shaft;
a first planetary gear assembly operably coupled to the main sun gear such that the first planetary gear assembly rotates about the longitudinal axis in response to a rotation of the main sun gear;
a second planetary gear assembly operably coupled to the first planetary gear assembly such that the second planetary gear assembly rotates in response to the rotation of the first planetary gear assembly;
a drive shaft having a proximal end portion coupled to the second planetary gear assembly for concomitant rotation therewith;
a high-speed output configured to rotate the actuation rod, the high-speed output coupled to the drive shaft for concomitant rotation therewith; and
a high-torque output configured to be operably coupled to a driven member of a surgical end effector, the high-torque output being operably coupled to the motor.

15. The powered surgical tack applier according to claim 14, wherein the high-speed output is concentrically disposed within the high-torque output.

16. The powered surgical tack applier according to claim 15, wherein the distal end portion of the drive shaft is disposed within and rotatable relative to the high-torque output.

17. The powered surgical tack applier according to claim 16, wherein the high-torque output defines a cavity therein, and the high-speed output is received in the cavity.

18. The powered surgical tack applier according to claim 14, wherein the gear box of the power module further includes a biasing member captured between the high-speed output and an inner surface of the high-torque output, wherein the biasing member is configured to distally-bias the high-speed output.

* * * * *